(12) United States Patent
Rousseau et al.

(10) Patent No.: US 8,678,008 B2
(45) Date of Patent: Mar. 25, 2014

(54) METHODS AND DEVICES FOR FORMING AN AUXILIARY AIRWAY FOR TREATING OBSTRUCTIVE SLEEP APNEA

(75) Inventors: Robert A. Rousseau, Ottsville, PA (US); Kevin Weadock, Hillsborough, NJ (US)

(73) Assignee: Ethicon, Inc, Somerville, NJ (US)

( * ) Notice: Subject to any disclaimer, the term of this patent is extended or adjusted under 35 U.S.C. 154(b) by 588 days.

(21) Appl. No.: 12/182,402

(22) Filed: Jul. 30, 2008

(65) Prior Publication Data

US 2010/0024830 A1  Feb. 4, 2010

(51) Int. Cl.
*A61F 5/56* (2006.01)

(52) U.S. Cl.
USPC .............................. 128/848; 623/9

(58) Field of Classification Search
USPC ........ 128/848; 623/9, 1.11, 1.23, 1.27; 604/8, 604/9, 11–18
See application file for complete search history.

(56) References Cited

U.S. PATENT DOCUMENTS

| | | |
|---|---|---|
| 3,123,077 A | 3/1964 | Alcamo |
| 3,378,010 A | 4/1968 | Codling et al. |
| 4,069,825 A | 1/1978 | Akiyama |
| 4,290,763 A | 9/1981 | Hurst |
| 4,557,264 A | 12/1985 | Hinsch |
| 4,839,215 A | 6/1989 | Starling et al. |
| 4,881,939 A | 11/1989 | Newman |
| 4,950,285 A | 8/1990 | Wilk |
| 5,053,047 A | 10/1991 | Yoon |
| 5,123,913 A | 6/1992 | Wilk et al. |
| 5,192,271 A | 3/1993 | Kalb et al. |
| 5,269,783 A | 12/1993 | Sander |
| 5,284,161 A | 2/1994 | Karell |
| 5,311,028 A | 5/1994 | Glavish |
| 5,393,984 A | 2/1995 | Glavish |
| 5,483,077 A | 1/1996 | Glavish |
| 5,484,444 A * | 1/1996 | Braunschweiler et al. .. 623/1.11 |

(Continued)

FOREIGN PATENT DOCUMENTS

| | | |
|---|---|---|
| CN | 2465680 | 12/2001 |
| DE | 10245076 | 4/2004 |

(Continued)

OTHER PUBLICATIONS

The Pillar Procedure, Restore Medical, Inc., www.restoremedical.com, 2 pp.

(Continued)

*Primary Examiner* — Patricia Bianco
*Assistant Examiner* — Keri J Nelson

(57) ABSTRACT

An auxiliary airway for treating obstructive sleep apnea is formed by implanting an elongated conduit beneath a pharyngeal wall of a pharynx. The elongated conduit has a proximal end in communication with a first region of the pharynx, a distal end in communication with a second region of the pharynx, and a section extending beneath the pharyngeal wall for bypassing an oropharynx region of the pharynx. The system includes a first opening in the pharyngeal wall in communication with a first opening in the elongated conduit, and a second opening in the pharyngeal wall in communication with a second opening in the elongated conduit. The system has a first anastomotic connector for coupling the first opening in the pharyngeal wall with the first opening in the conduit, and a second anastomotic connector for coupling the second opening in the pharyngeal wall with the second opening in the conduit.

24 Claims, 15 Drawing Sheets

(56) References Cited

U.S. PATENT DOCUMENTS

| | | |
|---|---|---|
| 5,609,559 A | 3/1997 | Weitzner |
| 5,683,417 A | 11/1997 | Cooper |
| 5,704,895 A | 1/1998 | Scott et al. |
| 5,792,067 A | 8/1998 | Karell |
| 5,843,077 A | 12/1998 | Edwards |
| 5,931,855 A | 8/1999 | Buneke |
| 6,161,541 A | 12/2000 | Woodson |
| 6,190,401 B1 | 2/2001 | Green et al. |
| 6,241,747 B1 | 6/2001 | Ruff |
| 6,250,307 B1 | 6/2001 | Conrad et al. |
| 6,348,156 B1 | 2/2002 | Vishnoi et al. |
| 6,431,174 B1 | 8/2002 | Knudson et al. |
| 6,432,437 B1 | 8/2002 | Hubbard |
| 6,457,472 B1 | 10/2002 | Schwartz et al. |
| 6,513,530 B2 | 2/2003 | Knudson et al. |
| 6,523,542 B2 | 2/2003 | Knudson et al. |
| 6,578,580 B2 | 6/2003 | Conrad et al. |
| 6,589,549 B2 | 7/2003 | Shih et al. |
| 6,599,310 B2 | 7/2003 | Leung et al. |
| 6,627,600 B2 | 9/2003 | Boutignon |
| 6,634,362 B2 | 10/2003 | Conrad et al. |
| 6,638,284 B1 | 10/2003 | Rousseau et al. |
| 6,716,251 B1 | 4/2004 | Asius et al. |
| 6,742,524 B2 | 6/2004 | Knudson et al. |
| 6,755,868 B2 | 6/2004 | Rousseau |
| 6,800,082 B2 | 10/2004 | Rousseau |
| 6,899,105 B2 | 5/2005 | Krueger et al. |
| 6,955,172 B2 | 10/2005 | Nelson et al. |
| 6,981,944 B2 | 1/2006 | Jamiolkowski et al. |
| 7,017,582 B2 | 3/2006 | Metzger et al. |
| 7,056,331 B2 | 6/2006 | Kaplan et al. |
| 7,135,189 B2 | 11/2006 | Knapp |
| 7,146,981 B2 | 12/2006 | Knudson et al. |
| 7,166,570 B2 | 1/2007 | Hunter et al. |
| 7,213,599 B2 | 5/2007 | Conrad et al. |
| 7,237,554 B2 | 7/2007 | Conrad et al. |
| 7,261,702 B1 | 8/2007 | Alexandre et al. |
| 7,288,075 B2 | 10/2007 | Parihar et al. |
| 7,297,102 B2 | 11/2007 | Smith et al. |
| 7,322,993 B2 | 1/2008 | Metzger et al. |
| 7,337,781 B2 | 3/2008 | Vassallo |
| 7,360,432 B2 | 4/2008 | Lehtonen |
| 7,360,542 B2 | 4/2008 | Nelson et al. |
| 7,367,340 B2 | 5/2008 | Nelson et al. |
| 7,401,611 B2 | 7/2008 | Conrad et al. |
| 7,442,389 B2 | 10/2008 | Quelle et al. |
| 7,601,164 B2 | 10/2009 | Wu |
| 7,669,603 B2 | 3/2010 | Knudson et al. |
| 7,806,908 B2 | 10/2010 | Ruff |
| 7,850,894 B2 | 12/2010 | Lindh, Sr. et al. |
| 7,857,829 B2 | 12/2010 | Kaplan et al. |
| 7,888,119 B2 | 2/2011 | Sugaya et al. |
| 8,142,422 B2 | 3/2012 | Makower et al. |
| 8,307,831 B2 | 11/2012 | Rousseau |
| 8,413,661 B2 | 4/2013 | Rousseau et al. |
| 2001/0037133 A1 | 11/2001 | Knudson et al. |
| 2002/0144685 A1 | 10/2002 | Ivanovich et al. |
| 2003/0004579 A1 | 1/2003 | Rousseau et al. |
| 2003/0034312 A1 | 2/2003 | Unger et al. |
| 2003/0149445 A1 | 8/2003 | Knudson et al. |
| 2003/0149447 A1 | 8/2003 | Morency et al. |
| 2003/0149488 A1 | 8/2003 | Metzger et al. |
| 2003/0176875 A1 | 9/2003 | Anderson et al. |
| 2004/0020492 A1 | 2/2004 | Dubrul et al. |
| 2004/0020498 A1 | 2/2004 | Knudson et al. |
| 2004/0028676 A1 | 2/2004 | Klein et al. |
| 2004/0102796 A1* | 5/2004 | Hill et al. ............... 606/153 |
| 2004/0139975 A1 | 7/2004 | Nelson et al. |
| 2004/0144395 A1 | 7/2004 | Evans et al. |
| 2004/0147811 A1 | 7/2004 | Diederich et al. |
| 2004/0149290 A1 | 8/2004 | Nelson et al. |
| 2004/0153127 A1 | 8/2004 | Gordon et al. |
| 2004/0231678 A1 | 11/2004 | Fierro |
| 2005/0038472 A1 | 2/2005 | Furst |
| 2005/0082452 A1 | 4/2005 | Kirby |
| 2005/0092334 A1 | 5/2005 | Conrad et al. |
| 2005/0115572 A1 | 6/2005 | Brooks et al. |
| 2005/0121039 A1 | 6/2005 | Brooks et al. |
| 2005/0159637 A9 | 7/2005 | Nelson et al. |
| 2005/0165352 A1* | 7/2005 | Henry et al. ............... 604/108 |
| 2005/0199248 A1 | 9/2005 | Pflueger et al. |
| 2005/0203576 A1 | 9/2005 | Sulamanidze |
| 2005/0251255 A1 | 11/2005 | Metzger et al. |
| 2005/0267321 A1 | 12/2005 | Shadduck |
| 2005/0267531 A1 | 12/2005 | Ruff et al. |
| 2005/0267532 A1 | 12/2005 | Wu |
| 2005/0267571 A1 | 12/2005 | Spence et al. |
| 2005/0279365 A1 | 12/2005 | Armijo et al. |
| 2006/0005843 A9 | 1/2006 | Nelson et al. |
| 2006/0079935 A1 | 4/2006 | Kolster |
| 2006/0083767 A1 | 4/2006 | Deusch et al. |
| 2006/0093644 A1 | 5/2006 | Quelle et al. |
| 2006/0150986 A1 | 7/2006 | Roue et al. |
| 2006/0185673 A1 | 8/2006 | Critzer et al. |
| 2006/0206197 A1 | 9/2006 | Morsi |
| 2006/0207608 A1 | 9/2006 | Hirotsuka et al. |
| 2006/0207612 A1 | 9/2006 | Jackson et al. |
| 2006/0228391 A1 | 10/2006 | Seyedin et al. |
| 2006/0241339 A1 | 10/2006 | Cook et al. |
| 2006/0266369 A1 | 11/2006 | Atkinson |
| 2006/0289015 A1 | 12/2006 | Boucher et al. |
| 2007/0000497 A1 | 1/2007 | Boucher et al. |
| 2007/0005109 A1 | 1/2007 | Popadiuk et al. |
| 2007/0005110 A1 | 1/2007 | Collier et al. |
| 2007/0102004 A1 | 5/2007 | Nelson et al. |
| 2007/0102010 A1 | 5/2007 | Lemperle et al. |
| 2007/0110788 A1 | 5/2007 | Hissong et al. |
| 2007/0119463 A1 | 5/2007 | Nelson et al. |
| 2007/0123996 A1 | 5/2007 | Sugaya et al. |
| 2007/0144531 A1 | 6/2007 | Tomas et al. |
| 2007/0144534 A1 | 6/2007 | Mery et al. |
| 2007/0144535 A1 | 6/2007 | Hegde et al. |
| 2007/0190108 A1 | 8/2007 | Datta et al. |
| 2007/0204866 A1 | 9/2007 | Conrad et al. |
| 2007/0209665 A1 | 9/2007 | Gillis et al. |
| 2007/0227545 A1 | 10/2007 | Conrad et al. |
| 2007/0233276 A1 | 10/2007 | Conrad et al. |
| 2007/0246052 A1 | 10/2007 | Hegde et al. |
| 2007/0256693 A1 | 11/2007 | Paraschac et al. |
| 2007/0257395 A1 | 11/2007 | Lindh et al. |
| 2007/0261701 A1 | 11/2007 | Sanders |
| 2007/0270631 A1 | 11/2007 | Nelson et al. |
| 2007/0272257 A1 | 11/2007 | Nelson et al. |
| 2007/0288057 A1 | 12/2007 | Kuhnel |
| 2007/0295338 A1 | 12/2007 | Loomas et al. |
| 2007/0295340 A1 | 12/2007 | Buscemi |
| 2008/0023012 A1 | 1/2008 | Dineen et al. |
| 2008/0035158 A1 | 2/2008 | Pflueger et al. |
| 2008/0035160 A1 | 2/2008 | Woodson et al. |
| 2008/0066764 A1 | 3/2008 | Paraschac et al. |
| 2008/0066765 A1 | 3/2008 | Paraschac et al. |
| 2008/0066767 A1 | 3/2008 | Paraschac et al. |
| 2008/0066769 A1 | 3/2008 | Dineen et al. |
| 2008/0078411 A1 | 4/2008 | Buscemi et al. |
| 2008/0146868 A1 | 6/2008 | Henri Robert et al. |
| 2008/0167614 A1* | 7/2008 | Tolkowsky et al. ........... 604/131 |
| 2008/0199248 A1 | 8/2008 | Hargadon |
| 2008/0208265 A1 | 8/2008 | Frazier et al. |
| 2008/0221684 A1 | 9/2008 | Nelson et al. |
| 2008/0312688 A1 | 12/2008 | Nawrocki et al. |
| 2009/0025734 A1 | 1/2009 | Doelling et al. |
| 2009/0078411 A1 | 3/2009 | Kenison et al. |
| 2009/0165803 A1 | 7/2009 | Bhat et al. |
| 2010/0023055 A1 | 1/2010 | Rousseau |
| 2010/0024830 A1 | 2/2010 | Rousseau et al. |
| 2010/0030011 A1 | 2/2010 | Weadock et al. |
| 2010/0037901 A1 | 2/2010 | Rousseau et al. |
| 2010/0080791 A1 | 4/2010 | Rousseau et al. |
| 2010/0106246 A1 | 4/2010 | Rousseau et al. |
| 2010/0108077 A1 | 5/2010 | Lindh et al. |
| 2010/0132719 A1 | 6/2010 | Jacobs et al. |
| 2010/0137794 A1 | 6/2010 | Knudson et al. |
| 2010/0137905 A1 | 6/2010 | Weadock et al. |
| 2010/0163056 A1 | 7/2010 | Tschopp et al. |

(56) References Cited

U.S. PATENT DOCUMENTS

| | | |
|---|---|---|
| 2010/0211184 A1 | 8/2010 | Rousseau et al. |
| 2010/0234794 A1 | 9/2010 | Weadock et al. |
| 2010/0234946 A1 | 9/2010 | Rousseau |
| 2010/0294284 A1 | 11/2010 | Hohenhorst et al. |
| 2010/0319710 A1 | 12/2010 | Sharkawy et al. |
| 2011/0100376 A1 | 5/2011 | Rousseau |
| 2011/0100377 A1 | 5/2011 | Weadock et al. |
| 2011/0100378 A1 | 5/2011 | Rousseau |
| 2011/0144558 A1 | 6/2011 | Rousseau |
| 2011/0174315 A1 | 7/2011 | Zhang et al. |
| 2011/0178439 A1 | 7/2011 | Irwin et al. |
| 2012/0123449 A1 | 5/2012 | Schaller et al. |
| 2012/0245629 A1 | 9/2012 | Gross et al. |
| 2013/0074849 A1 | 3/2013 | Rousseau et al. |
| 2013/0098371 A1 | 4/2013 | Rousseau et al. |
| 2013/0118505 A1 | 5/2013 | Rousseau et al. |
| 2013/0133669 A1 | 5/2013 | Rousseau |
| 2013/0150872 A1 | 6/2013 | Rousseau |
| 2013/0174857 A1 | 7/2013 | Rousseau et al. |
| 2013/0186412 A1 | 7/2013 | Weadock et al. |

FOREIGN PATENT DOCUMENTS

| | | |
|---|---|---|
| EP | 2145587 | 1/2010 |
| EP | 2517633 | 10/2012 |
| FR | 2651113 | 3/1991 |
| JP | 2001-145646 | 5/2001 |
| JP | 2003265621 | 9/2003 |
| RU | 2005447 | 1/1994 |
| RU | 2202313 | 4/2003 |
| SU | 927236 | 5/1982 |
| SU | 1697792 | 12/1991 |
| WO | 9713465 | 4/1997 |
| WO | 9900058 | 1/1999 |
| WO | 0066050 | 11/2000 |
| WO | 0121107 | 3/2001 |
| WO | 03096928 | 11/2003 |
| WO | 2004016196 | 2/2004 |
| WO | 2004020492 | 3/2004 |
| WO | 2004021869 | 3/2004 |
| WO | 2004021870 | 3/2004 |
| WO | 2004060311 | 7/2004 |
| WO | 2004084709 | 10/2004 |
| WO | 2005046554 | 5/2005 |
| WO | 2005051292 | 6/2005 |
| WO | 2005082452 | 9/2005 |
| WO | 2005122954 | 12/2005 |
| WO | 2006012188 | 2/2006 |
| WO | 2006072571 | 7/2006 |
| WO | 2006108145 | 10/2006 |
| WO | 2007056583 | 5/2007 |
| WO | 2007075394 | 7/2007 |
| WO | 2007132449 | 11/2007 |
| WO | 2007134005 | 11/2007 |
| WO | 2007146338 | 12/2007 |
| WO | 2007149469 | 12/2007 |
| WO | 2008118913 | 10/2008 |
| WO | 2009023256 | 2/2009 |
| WO | 2009036094 | 3/2009 |
| WO | 2010019376 | 2/2010 |
| WO | 2010035303 | 4/2010 |
| WO | 2010065341 | 6/2010 |
| WO | 2012041205 | 4/2012 |
| WO | 2012064902 | 5/2012 |
| WO | 2012170468 | 12/2012 |

OTHER PUBLICATIONS

Repose Genioglossus Advancement, INFLUENT Medical, www.influ-ent.com, 1 page.
Cole et al., "Snoring: A Review and a Reassessment", J. of Otolaryngology, pp. 303-306 (1995).
Harries et al., "The Surgical treatment of snoring", J. of Laryngology and Otology., pp. 1105-1106 (1996).
Huang et al., "Biomechanics of snoring", Endeavour, vol. 19(3): pp. 96-100 (1995).
Pang. Kenny et al., "Tongue Suspension Suture in Obstructive Sleep Apnea", Operative Techniques in Otolaryngology, vol. 17, No. 4, Dec. 2006, pp. 252-256.
Schwab et al., "Upper airway and soft tissue changes induced by CPAP in normal subject", Am. J. Respit. Crit. Care Med., vol. 154, No. 4, Oct. 1996, pp. 1106-1116.
Schwartz et al., "Effects of electrical stimulation to the soft palate on snoring and obstructive sleep apnea", J. Prosthetic Dentistry, pp. 273-281 (1986).
Shamsuzzaman et al., "Obstructive Sleep Apnea; Implications for Cardiac and Vascular Disease", JAMA vol. 290 (14): pp. 1906-1914.
Teles et al., "Use of Palatal Lift Prosthesis on Patent Submitted to Maxillectomy: A Case Report", Applied Cancer Res. 2005, vol. 25(3), pp. 151-154.
The Advance System, Aspire Medical, Inc. www.aspiremedical.com, 3 pp (2008).
The pillar Procedure. Restore Medical, Inc. www.restoremedical.com, 2 pp (2008).
Vicente et al., "Tongue-Base Suspension in Conjunction with Uvutopapatopharyngoplasty for Treatement of Severe Obstructive Sleep Apnea: Long-term Follow-Up Results", The Laryngoscope, vol. 115(7), pp. 1223-1227 (2006).
Wassmuth et al., "Cautery-assisted palatal stiffening operation for the treatment of obstructive sleep apnea syndrome", Otolaryngology—Head and Neck Surgery, vol. 123(1), pp. 55-60 (Jul. 2000).
Wiltfang et al., "First results on daytime submandibular electrostimulation of suprahyoidal muscles to prevent night-time hypopharyngeal collapse in obstructive sleep apnea syndrom", Intl J. of Oral & Maxillofacial Surgery, pp. 21-25 (1999).
Notification of Transmittal of the International Search Report and the Written Opinion of the International Search Authority or the Declaration mailed on Feb. 3, 2010, PCT/US2009/051921; International Filing Date: Jul. 28, 2009.
Notification of Transmittal of the International Search Report and the Written Opinion of the International Search Authority or the Declaration mailed on May 25, 2010, PCT/US2010/023152; International Filing Date: Apr. 2, 2010.
International Search Report dated Nov. 4, 2009 for International Patent Application No. PCT/US2009/052126.
International Search Report dated Dec. 21, 2009 for International Patent Application No. PCT/US2009/057661.
International Search Report dated Dec. 22, 2009 for International Patent Application No. PCT/US2009/061223.
International Search Report dated Apr. 29, 2010 for International Patent Application No. PCT/US2009/065293.
International Search Report dated May 25, 2010 for International Patent Application No. PCT/US2010/025778.
Database WPI Week 198312, Thomson Scientific, London, GB; AN 1983-D9513K XP002693421, -& SU 927 236 A1 (Petrozazodsk Univ) May 15, 1982 abstract (see figures 7 & 8).
Medtronic AIRvance System for Obstructive Sleep Apnea. http://www.medtronic.com/for-healthcare-professionals/products-therapies/ear-nose-throat/sleep-disordered-breathing-products/airvance-system-for-obstructive-sleep-apnea/index.htm, dated Oct. 9, 2013.
International Search Report dated May 25, 2010 for International Patent Application No. PCT/US2010/023152.
International Search Report dated Apr. 9, 2013 for International Patent Application No. PCT/US2012/061569.
International Search Report dated Apr. 2, 2013 for International Patent Application No. PCT/US2012/067708.
Written Opinion dated Nov. 27, 2012 for International Patent Application No. PCT/US2012/056577.

* cited by examiner

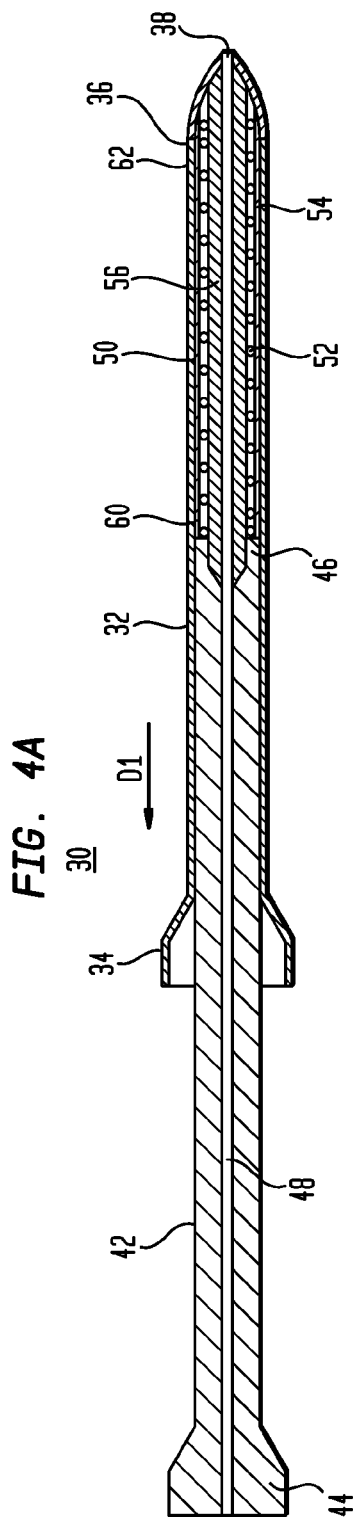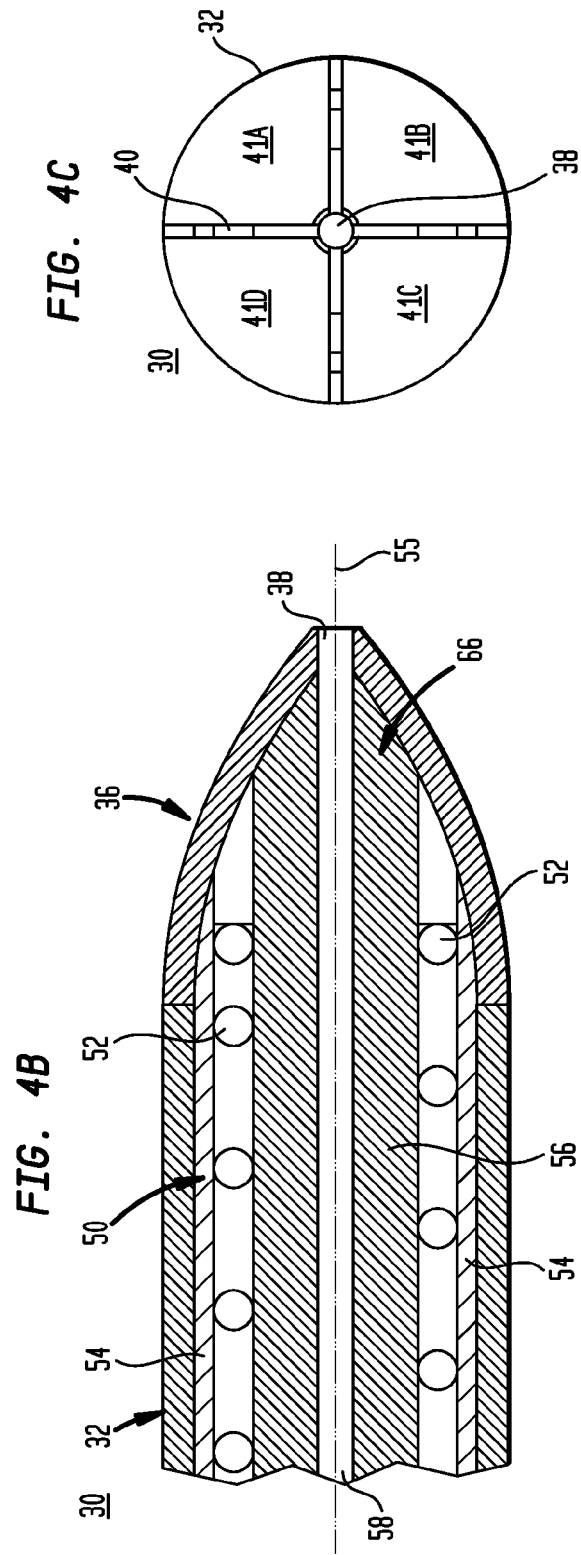

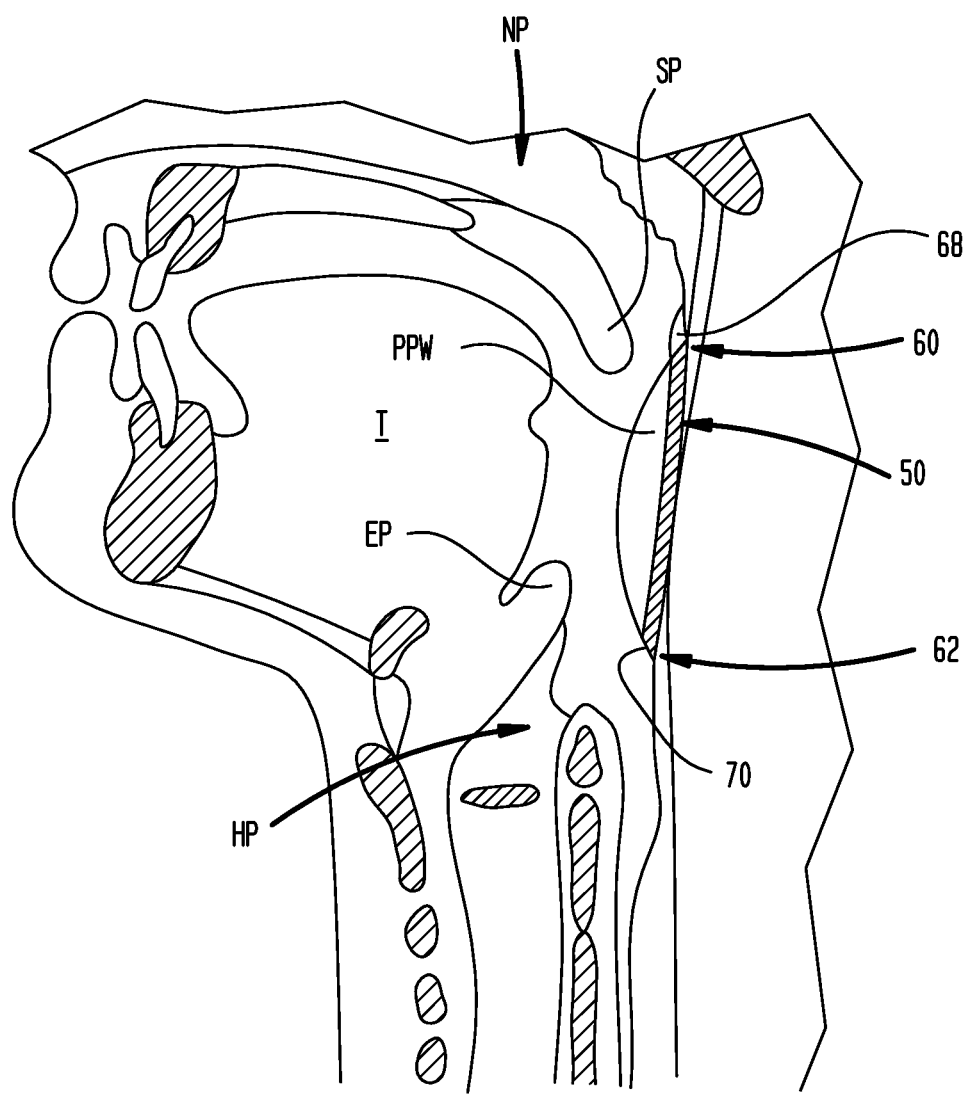

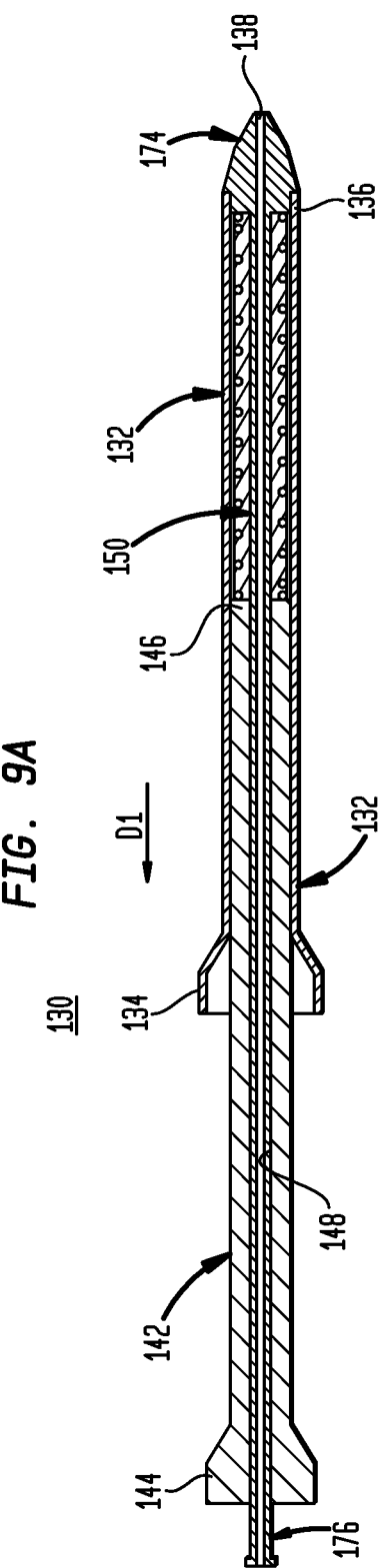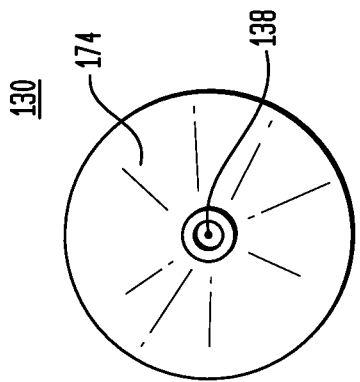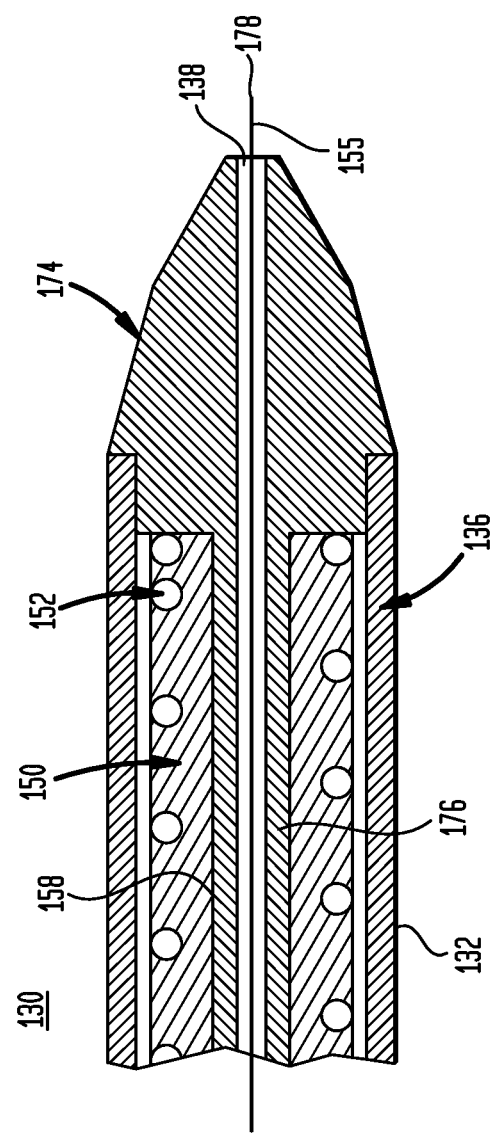

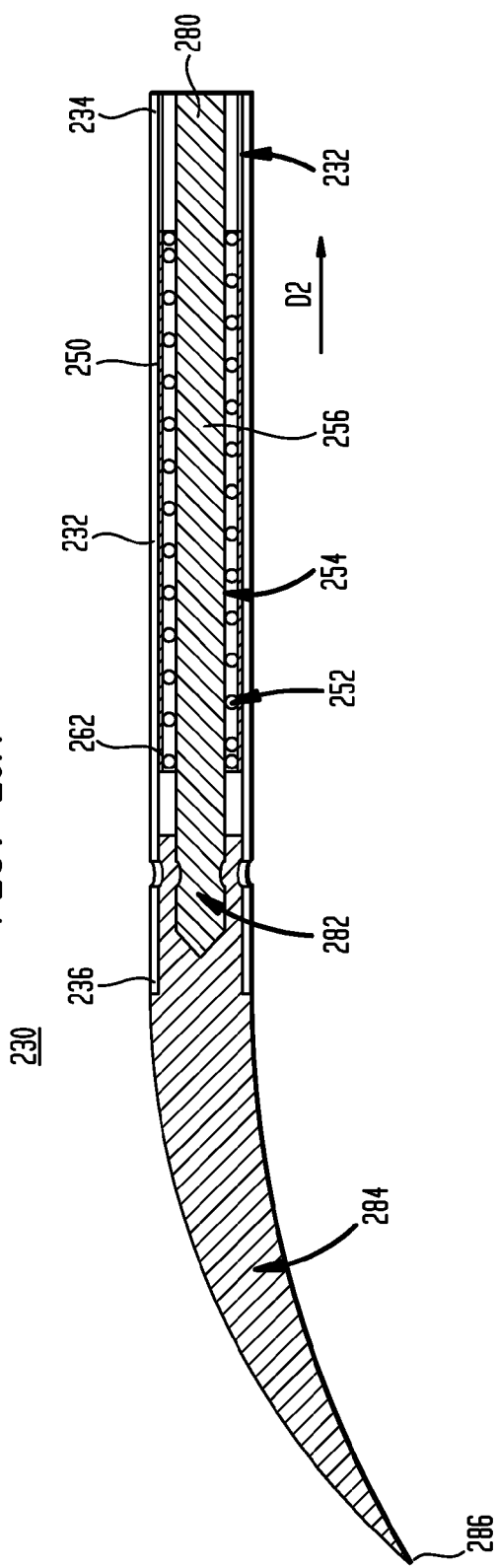
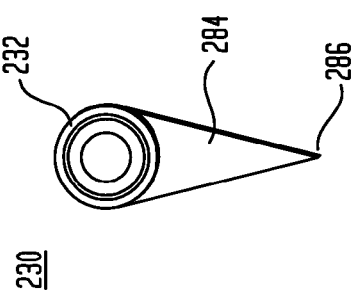
FIG. 10A
FIG. 10B

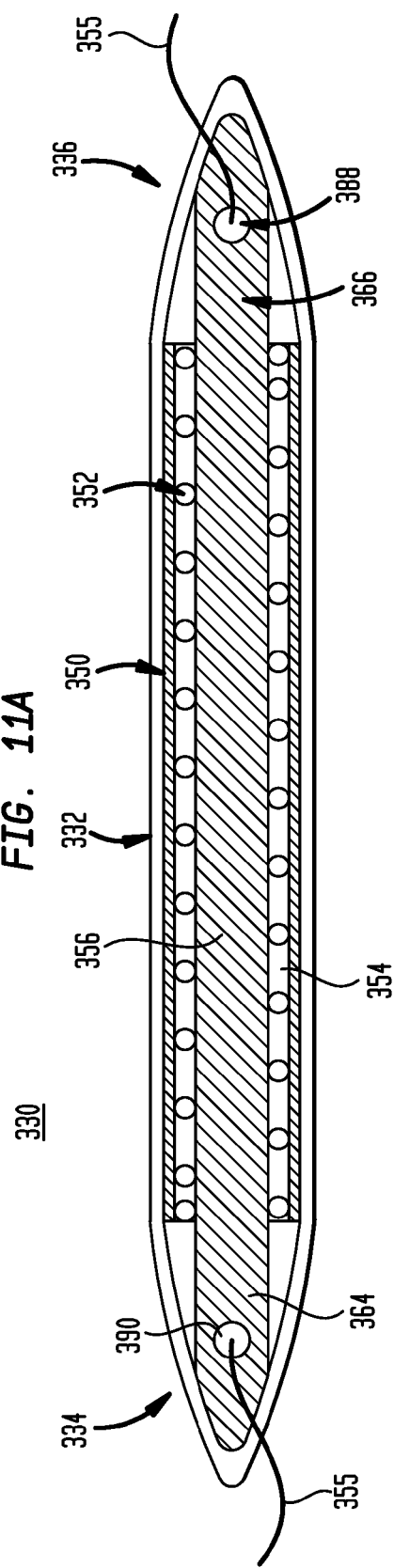

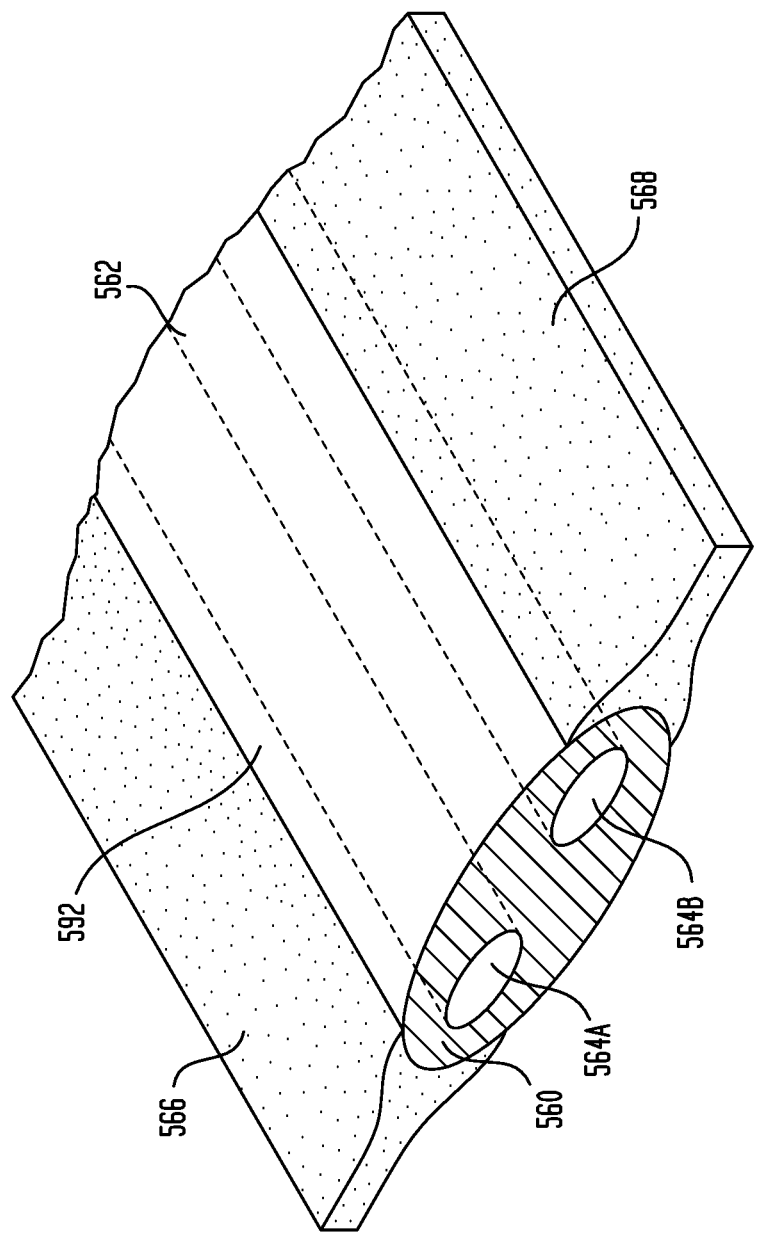

METHODS AND DEVICES FOR FORMING AN AUXILIARY AIRWAY FOR TREATING OBSTRUCTIVE SLEEP APNEA

BACKGROUND OF THE INVENTION

1. Field of the Invention

The present invention generally relates to treating sleep disorders, and more specifically relates to methods and devices for forming auxiliary airways for treating patients suffering from obstructive sleep apnea and hypopnea.

2. Description of the Related Art

Obstructive sleep apnea (OSA) is caused by a blockage of the airway, which usually occurs when the soft tissue in the throat collapses and closes during sleep. During each apnea event, the brain briefly arouses the sufferer in order to initiate the resumption of breathing, however, this type of sleep is extremely fragmented and of poor quality. When left untreated, sleep apnea may result in high blood pressure, cardiovascular disease, weight gain, impotency, headaches, memory problems, job impairment, and motor vehicle crashes.

According to the National Institutes of Health, OSA is rather common and affects more than twelve million Americans. OSA affects males more than females. Other risk factors include being overweight, and being over the age of forty, however, sleep apnea can strike anyone at any age, even children. Despite the seriousness of OSA, a lack of awareness by the public and healthcare professionals results in the vast majority of patients remaining undiagnosed and untreated.

There have been a number of efforts directed to treating OSA. For example, devices for electrically stimulating the soft palate to treat snoring and obstructive sleep apnea are disclosed in U.S. Pat. Nos. 5,284,161 and 5,792,067. These devices have had mixed results because they require patient adherence to a regimen of use, subject the patient to discomfort during sleep, and result in repeated arousal of the patient.

Surgical treatments have also been employed. One such treatment is referred to as uvulopalatopharyngoplasty, which involves removing about 2 cm of the trailing edge of the soft palate to reduce the soft palate's ability to flutter between the tongue and the pharyngeal wall of the throat. The procedure has been effective in alleviating snoring, but is painful and frequently results in undesirable side effects. In particular, removal of the trailing edge of the soft palate compromises the soft palate's ability to seal off nasal passages during swallowing and speech. As a result, in 25% of uvulopalatopharyngoplasty patients, fluid escapes from the mouth and flows into the nose while drinking.

Another procedure uses a surgical laser to create scar tissue on the surface of the soft palate. The scar tissue reduces the flexibility of the soft palate, which, in turn, reduces snoring and/or closing of the air passage.

Cautery-assisted palatal stiffening operation (CAPSO) is a recently developed office-based procedure performed with local anesthesia. A midline strip of soft palate mucosa is removed, and the wound is allowed to heal. The flaccid palate is stiffened, and palatal snoring ceases.

Surgical procedures such as uvulopalatopharyngoplasty and those mentioned above continue to have problems. The area of surgical treatment (i.e., removal of palatal tissue or scarring of palatal tissue) may be more than is necessary to treat the patient's condition. In addition, the proposed procedures are painful with extended and uncomfortable healing periods. For example, scar tissue on the soft palate may present a continuing irritant to the patient. Moreover, the procedures are not reversible in the event they happen to induce adverse side effects.

Continuous positive airway pressure (CPAP), which delivers air into the airway through a specially designed nasal mask or pillow, has been adopted as a treatment for sleep apnea. The flow of air creates positive pressure when the patient inhales to keep the airway open. CPAP is considered by many to be the most effective non-surgical treatment for the alleviation of snoring and obstructive sleep apnea, however, patients complain about discomfort from the mask and hoses, including bloating, nasal drying, and dry eyes. As a result, patient compliance is only about 40%.

Other surgical approaches have been tried that employ the use of RF or microwave energy (Somnoplasty) to shrink tissue in the tongue or soft palate. Radiofrequency ablation of the soft palate is used to produce thermal lesions within the tissues. Somnoplasty devices have been approved by the U.S. Food and Drug Administration (FDA) for radiofrequency ablation of palatal tissues for simple snoring and for the base of the tongue for OSA. In some situations, radiofrequency of the soft palate and base of tongue are performed together as a multilevel procedure. To date, the treatments alone or in combination have failed to provide relief to more than 50% of patients.

Another device intended to treat snoring or obstructive sleep apnea uses several braided PET cylinders that are implanted to make the tissues of the tongue or uvula more rigid and less prone to deflection against the pharyngeal wall. The Pillar™ Palatal Implant System sold by Restore Medical of St. Paul, Minn. is an implantable device that has been cleared by the FDA. The device is a cylindrical-shaped segment of braided polyester filaments that is permanently implanted submucosally in the soft palate, for reducing the incidence of airway obstructions in patients suffering from mild to moderate obstructive sleep apnea. The Pillar device has been associated with a number of adverse side effects, including extrusion, infection, and patient discomfort.

Another implant system sold under the trademark REPOSE™ by InfluENT of Concord, N.H., uses a titanium screw that is inserted into the posterior aspect of the mandible at the floor of the mouth. A loop of suture is passed through the tongue base and attached to the mandibular bone screw. The Repose™ procedure achieves a suspension or hammock of the tongue base making it less likely for the base of the tongue to prolapse during sleep. Due to the high activity of the tongue during wakefulness, the suture component of this device has been shown to act as a "cheese cutter" to the tongue, causing device failure and requiring subsequent removal. Thus, the duration of beneficial effects afforded by the implant is less than a year.

Magnets have also been considered as implants for treating sleep apnea. These devices have shown limited success due to implant migration, inability to control the degree of tissue manipulation or treatment, and that the devices only provide temporary results.

In spite of the above efforts, no one device has been used to effectively treat obstructive sleep apnea. Thus, there remains a need for methods and devices that reduce the burden of managing obstructive sleep apnea through minimally invasive approaches that provide long term results, that encourage patient compliance, and that minimize patient discomfort.

SUMMARY OF THE INVENTION

The present invention is directed to methods and devices for forming an auxiliary airway between the nasopharynx and the hypopharynx, near, or into, the trachea to overcome problems associated with obstructive sleep apnea. In one embodiment, an auxiliary airway device is implanted in tissue outside the natural airway to provide an auxiliary airway between one site of the pharynx to another site, for example, the nasopharynx and the trachea. The auxiliary airway device preferably bypasses the soft tissue present in the oropharynx region (e.g. the soft palate, the epiglottis and the back of the tongue) that closes the natural airway during an obstructive sleep apnea episode. In one embodiment, the auxiliary airway device is implanted in tissue beneath the pharyngeal wall, such as the posterior or lateral pharyngeal wall. The auxiliary airway device may include a biocompatible conduit such as a stent or a biocompatible tube.

In one embodiment, the auxiliary airway device is implanted in tissue using an applicator or delivery instrument. The delivery instrument may be used to form an opening in the tissue and introduce the auxiliary airway device into the tissue. In one embodiment, the auxiliary airway device is an elongated conduit such as a stent that is slideably received over a flexible mandrel. In one embodiment, the distal end of the delivery instrument is tunneled beneath the pharyngeal wall at a proximal position within the nasopharynx region and at a distal position within the hypopharynx region proximate the trachea.

After the auxiliary airway device is implanted beneath the pharyngeal wall, a period of time (e.g. several weeks) is allowed to pass to provide for healing, tissue ingrowth into the device, and the formation of a mucosal surface. After the therapeutic period of time, the mandrel may be removed from the stent to define the new auxiliary airway. When the soft tissues of the pharynx such as the soft palate, the epiglottis, and/or the tongue block the normal airway through the pharynx, the auxiliary airway device allows for air flow to occur through the auxiliary airway extending between the nasopharynx and the hypopharynx. As such, the auxiliary airway device is useful for treating and overcoming problems associated with obstructive sleep apnea.

In one embodiment, any part of the surface of the auxiliary airway device may be impregnated or coated with an anti-inflammatory and/or an anti-microbial agent. The anti-inflammatory and anti-microbial agents preferably improve the acceptance of the device and minimize the likelihood of infection. In one embodiment, a sclerosing agent may be injected in or around the auxiliary airway device to promote the formation of scarring, which is believed to enhance the formation of the auxiliary airway between the nasopharynx and the hypopharynx. The sclerosing agent may also be coated onto any part or surface of the auxiliary airway. In another embodiment, energy such as RF energy may be introduced in and/or around the auxiliary airway device to promote scarring around the auxiliary airway device so as to form a stiff, scarred tunnel for supporting the auxiliary airway device.

In one embodiment, a method of treating obstructive sleep apnea includes forming an auxiliary airway extending beneath a pharyngeal wall. The auxiliary airway desirably has a proximal end in communication with a first region (e.g. the nasopharynx region) of a pharynx and a distal end in communication with a second region (e.g. the hypopharynx region) of the pharynx. Forming the auxiliary airway may include implanting an auxiliary airway device beneath the pharyngeal wall, the auxiliary airway device having a proximal end and a distal end with a first opening adjacent the proximal end and a second opening adjacent the distal. The method may include forming a first opening in the pharyngeal wall in communication with the first opening adjacent the proximal end of the auxiliary airway device, and forming a second opening in the pharyngeal wall in communication with the second opening adjacent the distal end of the auxiliary airway device. In one preferred embodiment, the auxiliary airway device extends through a lateral wall of the pharyngeal wall.

In one embodiment, a method of treating obstructive sleep apnea includes forming an auxiliary airway extending beneath a pharyngeal wall. A tunnel may be formed through tissue using well known techniques and a mandrel may be positioned within the tunnel beneath the tissue. In one embodiment, a sclerosing agent is used to stiffen the tissue surrounding the mandrel and within the tunnel. In another embodiment, energy such as RF energy may be used to create lesions surrounding the mandrel and within the tunnel. After healing, the mandrel is removed and the surrounding stiffened tissue or scar tissue acts to support the tissue of the auxiliary airway without requiring the use of an implant such as a stent or tube.

In one embodiment, a first anastomotic connector is used for coupling the first opening in the pharyngeal wall with the first opening adjacent to the proximal end of the auxiliary airway device. A second anastomotic connector may be used for coupling the second opening in the pharyngeal wall with the second opening adjacent to the distal end of the auxiliary airway device.

In one embodiment, the auxiliary airway device includes a main body portion and a central lumen extending through the main body portion between the proximal and distal ends of the device. The main body portion of the auxiliary airway device may have an elliptical or generally flattened cross-sectional shape. The first opening adjacent the proximal end of the auxiliary airway device may extend through a lateral wall of the main body portion and be in communication with the central lumen. The second opening adjacent the distal end of the auxiliary airway device may also extend through the lateral wall of the main body portion and be in communication with the central lumen. In one embodiment, the first and second openings are formed in a rear wall of the main body portion. The rear wall of the main body portion may be flat.

The implanting step may include positioning a mandrel within the central lumen of the auxiliary airway device, and after positioning the mandrel, inserting the auxiliary airway device and the mandrel beneath the pharyngeal wall. In one embodiment, the mandrel has a central lumen and a guidewire is passed through the central lumen for advancing the mandrel to an implant site. After a period of time for healing, the mandrel may be removed from the central lumen of the auxiliary airway device. In one embodiment, the mandrel may have multiple parts so that the different parts of the mandrel may be removed separately to minimize friction on the opening formed in the pharyngeal wall. In one embodiment, the mandrel may be inflated for supporting the auxiliary airway device during implantation of the device, and the mandrel may be deflated before removing the mandrel from the implanted auxiliary airway device to minimize friction.

In one embodiment, a system for treating obstructive sleep apnea includes an elongated conduit, such as a biocompatible stent or a biocompatible tube, implanted beneath a pharyngeal wall of a pharynx. The elongated conduit desirably has a proximal end in communication with a first region (e.g. the nasopharynx region) of the pharynx and a distal end in communication with a second region (e.g. the hypopharynx region) of the pharynx. The elongated conduit preferably includes an intermediate section that extends beneath the pharyngeal wall for bypassing an oropharynx region of the pharynx.

In one embodiment, the elongated conduit has a first opening adjacent the proximal end thereof and a second opening adjacent the distal end thereof. The system also desirably includes a first opening in the pharyngeal wall in communication with the first opening adjacent the proximal end of the elongated conduit, and a second opening in the pharyngeal wall in communication with the second opening adjacent the distal end of the elongated conduit.

In one embodiment, the elongated conduit is preferably selected from biocompatible conduits, stents, polymer tubes, and tubes. The elongated conduit preferably has a length of about 3-10 cm and a diameter of about 2-8 mm. The wall thickness may vary from about 0.1-2.0 mm. The elongated conduit desirably includes a central lumen extending between the proximal and distal ends thereof. A mandrel is preferably insertable within the central lumen of the elongated conduit for supporting the elongated conduit as the elongated conduit is implanted in tissue such as tissue beneath the pharyngeal wall. The mandrel may be removed at a later time.

In one embodiment, the system preferably includes a first anastomotic connector for coupling the first opening in the pharyngeal wall with the first opening adjacent the proximal end of the elongated conduit, and a second anastomotic connector for coupling the second opening in the pharyngeal wall with the second opening adjacent the distal end of the elongated conduit.

In one embodiment, an auxiliary airway device for treating obstructive sleep apnea includes an elongated conduit implanted in tissue, the elongated conduit having a first opening in communication with an opening in the nasopharynx region of a pharynx and a second opening in communication with an opening in the hypopharynx region of the pharynx. The elongated conduit is preferably implanted beneath a pharyngeal wall, and more preferably in a lateral section of the pharyngeal wall.

In one embodiment, the elongated conduit has a proximal end and a distal end, a proximal opening adjacent the proximal end thereof, and a distal opening adjacent the distal end thereof. The proximal opening is preferably in communication with a first opening in the pharyngeal wall located in the nasopharynx region of the pharynx and the distal opening is preferably in communication with a second opening in the pharyngeal wall located in the hypopharynx region of the pharynx.

The auxiliary airway device preferably includes a first anastomotic connector coupling the proximal opening of the elongated conduit and the first opening in the pharyngeal wall and a second anastomotic connector coupling the distal opening of the elongated conduit and the second opening in the pharyngeal wall.

The elongated conduit preferably has an intermediate section that is implanted beneath the pharyngeal wall. The intermediate section of the elongated conduit preferably bypasses the soft tissue within an oropharynx region of the pharynx.

In one embodiment, an elongated outer sheath may be positioned around the elongated conduit for facilitating implanting the elongated conduit in the tissue, and a mandrel may be disposed within the elongated conduit for supporting the elongated conduit during implanting the elongated conduit in the tissue.

In one embodiment, a system for treating obstructive sleep apnea includes an elongated conduit extending beneath a pharyngeal wall of a pharynx, whereby the elongated conduit has a proximal end in communication with a first region (e.g. the nasopharynx region) of the pharynx and a distal end in communication with a second region (e.g. the hypopharynx region) of the pharynx. An intermediate section of the elongated conduit preferably extends beneath the pharyngeal wall for bypassing the soft tissue likely to collapse to obstruct the airway and/or an oropharynx region of the pharynx.

In one embodiment, the elongated conduit has a first opening adjacent the proximal end of the conduit and a second opening adjacent to the distal end of the conduit. The system also includes a first opening in the pharyngeal wall in communication with the first opening adjacent the proximal end of the elongated conduit, and a second opening in the pharyngeal wall in communication with the second opening adjacent the distal end of the elongated conduit. The system also desirably includes a first anastomotic connector for coupling the first opening in the pharyngeal wall with the first opening adjacent the proximal end of the elongated conduit, and a second anastomotic connector for coupling the second opening in the pharyngeal wall with the second opening adjacent the distal end of the elongated conduit.

In one embodiment, the elongated conduit desirably includes a central lumen extending between the proximal and distal ends thereof. A mandrel may be insertable within the central lumen of the elongated conduit for supporting the elongated conduit as the elongated conduit is implanted beneath the pharyngeal wall. The elongated conduit is desirably selected from a group of structures including biocompatible conduits, stents, polymer tubes, and tubes.

In one embodiment, the elongated conduit is a stent that is implanted beneath tissue by first placing a mandrel within an elongated central lumen of the stent, and placing the stent and the mandrel within a sheath. The sheath is preferably used for tunneling beneath the tissue and forming an elongated opening for implanting the stent and the mandrel. After the sheath has been used to implant the stent and the mandrel, the sheath may be removed. The stent and the mandrel preferably remain in place in the tunnel formed in the tissue during a healing period. After the healing period is complete, the mandrel may be removed from the central lumen extending through the stent, with the stent remaining implanted in the tissue.

In one embodiment, a delivery instrument is not used for implanting the auxiliary airway device disclosed and described herein. In this embodiment, the auxiliary airway device may be implanted using a technique similar to a TVT style device whereby the stent/mandrel combination is pulled through the tissue using tunneling devices or blunt needles. In this particular embodiment, the auxiliary airway device may be passed from a central incision in the pharyngeal wall and pulled in opposing directions to position the stent/mandrel combination at the desired superior and inferior locations within the pharynx.

In one embodiment, the delivery instrument and/or the mandrel have lumens extending therethrough and a guide wire is passed through the lumens. The guide wire may be used for advancing the delivery instrument, the mandrel, and the auxiliary airway device to a desired location in tissue.

In one embodiment, a method of treating obstructive sleep apnea includes forming an auxiliary airway extending beneath a pharyngeal wall, the auxiliary airway having a proximal end in communication with a first region of a pharynx (e.g. the nasopharynx region) and a distal end in communication with a second region of the pharynx (e.g. the hypopharynx region). The auxiliary airway may be formed by implanting a mandrel beneath the pharyngeal wall, and exposing tissue surrounding the mandrel to a sclerosing agent or energy for stiffening the tissue. The method includes removing the mandrel after a period of time, whereby the stiffened tissue supports the auxiliary airway for maintaining the auxiliary airway open. In one embodiment, the sclerosing agent is coated onto an outer surface of the mandrel. In one embodiment, the mandrel is impregnated with or carries the sclerosing agent. In one embodiment, the energy used for stiffening the tissue may include electrical, ultrasound, thermal, and/or RF energy. The energy may be applied by connecting a conductive wire to the mandrel or applied externally.

The methods and devices disclosed herein allow for breathing to occur if and when the tongue or surrounding tissues cause obstruction of an airway. Accordingly, the device is useful in treating obstructive sleep apnea and other related sleep disorders.

These and other preferred embodiments of the present invention will be described in more detail below.

BRIEF DESCRIPTION OF THE DRAWING

FIGS. 4A-4C show an applicator instrument for implanting an auxiliary airway device, in accordance with one embodiment of the present invention.

FIG. 8 shows an auxiliary airway device implanted in a human head, in accordance with one embodiment of the present invention.

FIGS. 9A-9C show an applicator instrument for implanting an auxiliary airway device, in accordance with one embodiment of the present invention.

FIGS. 10A-10B show an applicator instrument for implanting an auxiliary airway device, in accordance with one embodiment of the present invention.

FIGS. 11A-11B show an applicator instrument for implanting an auxiliary airway device, in accordance with one embodiment of the present invention.

FIG. 16 shows an auxiliary airway device, in accordance with one embodiment of the present invention.

DETAILED DESCRIPTION

Figure 1:
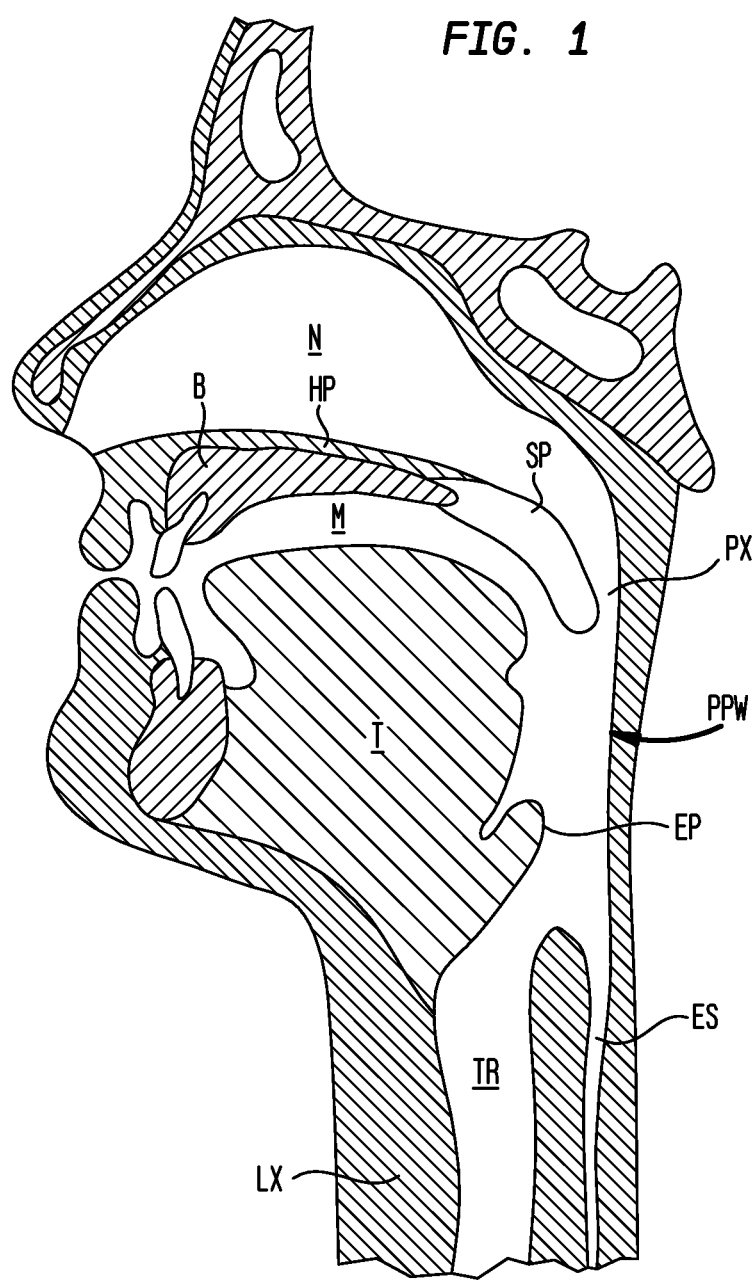
FIG. 1 shows a cross-sectional view of a human head including a nasal cavity and a pharynx.

FIG. 1 shows a cross-section of a human head with anatomical structures including the nasal cavity N, bone B of the hard palate HP, the soft palate SP, the mouth M, the tongue T, the trachea TR, the epiglottis EP, the esophagus ES, and the posterior pharyngeal wall PPW.

Figure 2:
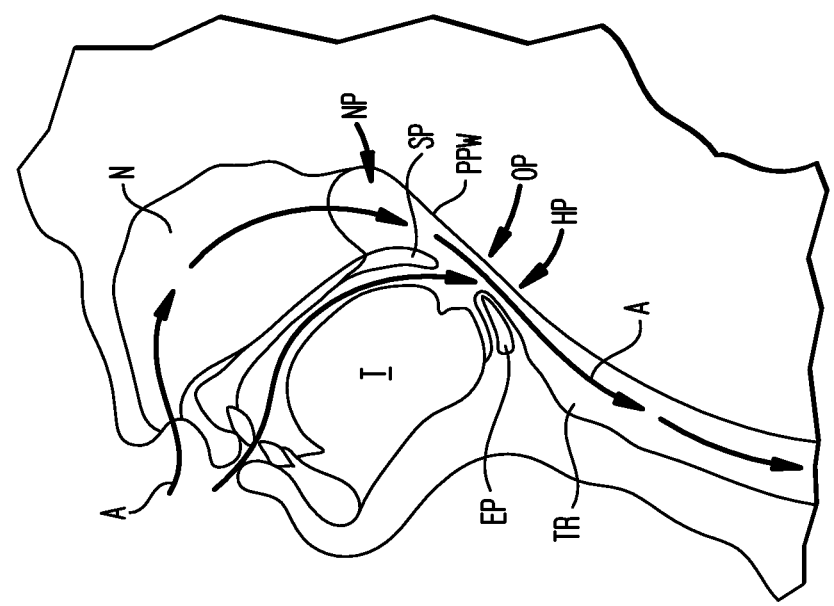
FIG. 2 shows a cross-sectional view of the nasal cavity and the pharynx of a human during normal breathing.

In a human body, an air filled space between the nasal cavity N and the larynx LX is referred to as the upper airway. The most critical part of the upper airway associated with sleep disorders is the pharynx PX. Referring to FIG. 2, the pharynx has three different anatomical levels. The nasopharynx NP is the upper portion of the pharynx located in the back of the nasal cavity N. The oropharynx OP is the intermediate portion of the pharynx containing the soft palate SP, the epiglottis EP, and the curve at the back of the tongue T. The hypopharynx HP is the lower portion of the pharynx located below the soft tissue of the oropharynx OP. The oropharynx OP is the section of the pharynx that is most likely to collapse due to the high prevalence of soft tissue structure, which leaves less space for airflow. The hypopharynx HP lies below the aperture of the larynx and behind the larynx, and extends to the esophagus.

As is well known to those skilled in the art, the soft palate and the tongue are both very flexible structures. The soft palate SP provides a barrier between the nasal cavity N and the mouth M. In many instances, the soft palate SP is longer than necessary so that it extends a significant distance between the back of the tongue T and the posterior pharyngeal wall PPW.

Figure 3:
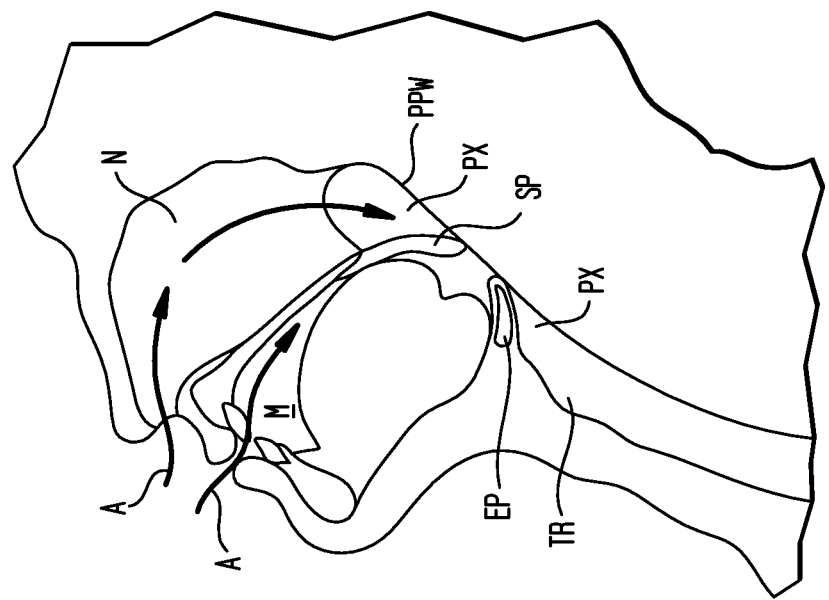
FIG. 3 shows a cross-sectional view of the nasal cavity and the pharynx of a human during an episode of obstructive sleep apnea.

Referring to FIG. 2, when an individual is awake, the back of the tongue T and the soft palate SP maintain their shape and tone due to their respective internal muscles. As a result, the airway A through the pharynx remains open and unobstructed. During sleep, however, the muscle tone decreases so that the back of the tongue and the soft palate become more flexible and distensible. Referring to FIG. 3, without normal muscle tone to keep their shape and to keep them in place either alone or as a group, the back of the tongue T, the epiglottis EP, and the soft palate SP tend to easily collapse to block the airway A.

Although the muscles relax throughout the body during sleep, most of the muscles of the respiratory system remain active. During inhalation, the diaphragm contracts and causes negative pressure to draw air A into the nasal cavity N and the mouth M. The air then flows past the pharynx PX, through the trachea TR and into the lungs. The negative pressure causes the tissue of the upper airway to deform slightly, which narrows the airway passage. In apneic patients, the soft palate SP, the tongue T, and/or the epiglottis EP collapse against the posterior pharyngeal wall PPW to block airflow into the trachea. As the airway narrows, airflow through the pharynx becomes turbulent which causes the soft palate SP to vibrate, generating a sound commonly known as snoring.

During sleep, humans typically experience brief obstructions of airflow and/or small decreases in the amount of airflow into the trachea and lungs. An obstruction of airflow for more than ten seconds is referred to as apnea. A decrease in airflow by more than fifty percent is referred to as hypopnea. The severity of sleep disorders is measured by the number of apneas and hypopneas that occur during every hour of sleep.

If apnea or hypopnea occurs more than five times per hour, most medical personnel diagnose the individual as having an upper airway resistance problem. Many of these patients often exhibit symptoms related to sleep disorders including sleepiness during the day, depression, and difficulty concentrating.

Individuals having ten or more episodes of apnea or hypopnea during every hour of sleep are officially classified as having obstructive sleep apnea syndrome. As the airway is obstructed, the individual makes repeated attempts to force inhalation. Many of these episodes are silent and are characterized by movements of the abdomen and chest wall as the individual strains to draw air into the lungs. Typically, episodes of apnea may last a minute or more. During this time, oxygen levels in the blood will decrease. Ultimately, the obstruction may be overcome by the individual generating a loud snore or awakening with a choking feeling.

In one embodiment, the present invention discloses devices and methods of forming an auxiliary airway or path to bypass restricted or obstructed areas of the pharynx. In one embodiment, the auxiliary airway is formed using an implantable auxiliary airway device such as a stent or porous tube that is implanted in tissue such as tissue below the pharyngeal wall. The device may include a stent that is slideably engaged with a flexible mandrel. The device is implanted behind the pharyngeal wall with a first end being located within the nasopharynx and a second end being located within the hypopharynx. The device preferably has a proximal opening in communication with the nasopharynx and a distal opening in communication with the hypopharynx. After implantation, tissue may grow into the porous spaces within the stent struts and between the mandrel and the stent itself so as to form a mucosal like surface. A mucosal surface will aid in the transit of mucous within the lumen in the auxiliary airway. After a healing period (e.g. three weeks), the mandrel may be removed from the device to provide for a new auxiliary airway between the nasopharynx and the hypopharynx. The auxiliary airway device preferably allows for breathing to occur even when the tongue or the surrounding soft tissues collapse into the airway or partially obstruct the airway. Additionally, the auxiliary airway may be sized to provide an alternate pathway that works in conjunction with a partially collapsed airway to minimize the likelihood of a complete airway collapse. In this embodiment, the auxiliary airway is sized to provide a minimum diameter self-supporting airway that prevents the formation of velocity induced pressure reduction within the upper airway.

Referring to FIGS. 4A-4C, in one embodiment, a system for forming an auxiliary airway includes an applicator instrument 30 having an outer sheath 32 with a proximal end 34 and a distal end 36. The distal end 36 of the outer sheath includes a central opening 38 and slits 40 extending outwardly from the central opening 38. The slits 40 preferably define flaps 41A-41D at the distal end 36 of the outer sheath 32 that are normally closed but that are adapted to flex away from one another to provide a larger opening for deploying an auxiliary airway device.

The applicator instrument 30 includes a pusher 42 insertable into the outer sheath 32. The pusher 42 has a proximal end 44, a distal end 46 and a central lumen 48 extending between the proximal and distal ends thereof. The applicator instrument 30 also includes an auxiliary airway device such as a stent 50 positioned near the distal end 36 of the outer sheath 32. In one embodiment, the stent 50 preferably includes a stent strut 52 and a stent graft 54 covering the stent strut. A mandrel 56, disposed inside the stent 50, has a central lumen 58 extending along the length thereof. The central lumen 58 of the mandrel 56 is in communication with the central opening 38 at the distal end 36 of the outer sheath 32. When the mandrel 56 is positioned within the outer sheath 32, and the distal end 46 of the pusher 42 is coupled with a proximal end of the mandrel 56, the central lumen 48 of the pusher 42 is preferably aligned with both the central lumen 58 of the mandrel 56 and the central opening 38 at the distal end of the outer sheath 32.

FIG. 4B shows an expanded view of the distal end of the applicator instrument 30 including the distal end 36 of the outer sheath 32. The stent 50, including the stent strut 52 and the stent graft 54, is disposed within the outer sheath 32, and the mandrel 56 is disposed inside the stent 50. The central lumen 58 of the mandrel 56 is preferably aligned with the central opening 38 at the distal end 36 of the outer sheath 32. Referring to FIG. 4A, in one embodiment, the stent 50 has a proximal end 60 and a distal end 62. The stent 50 is preferably flexible. In one embodiment, the stent has a length of approximately 3-15 cm and a diameter of 2-8 mm.

Referring to FIG. 4B, in one embodiment, a guide wire 55 is passed through target tissue. The guide wire 55 may be passed through the tissue by first forming a tunnel in the tissue and then passing the guide wire through the tunnel. In one embodiment, a needle (not shown) may be attached to a leading end of the guide wire 55 and the needle may be pulled through the tissue for deploying the guide wire. The central lumens 48, 58 of the respective pusher 42 and mandrel 56 are advanced over the guide wire 55 for positioning the stent 50 at a desired location within the tunnel formed in the tissue. Referring to FIG. 4A, once the stent 50 has been advanced along the guide wire to the predetermined position within the tissue, the stent 50 may be deployed from the distal end 36 of the outer sheath 32 by pulling the proximal end 34 of the outer sheath 32 in the direction designated $D_1$. As the outer sheath 32 is pulled toward the proximal end 44 of the pusher 42 in the direction designated $D_1$, the distal end 46 of the pusher 44 urges the stent 50 and the mandrel 56 toward the distal end of the outer sheath 32 and the flexible flaps 41A-41D (FIG. 4C) open for deploying the stent 50 in the tunnel formed in the tissue.

Referring to FIGS. 4A and 4B, in one embodiment, the mandrel 56 positioned within the stent 50. The mandrel 56 includes a proximal end 64 and a distal end 66, and is preferably flexible. The mandrel 56 preferably supports the stent 50 as the stent is implanted in tissue. The mandrel is preferably formed of biocompatible materials such as e-PTFE, PFTE, polypropylene, polyethylene, polyurethane, polycarbonate, or silicone and has a length of 3-20 cm and a diameter of 1-7 mm. In one embodiment, the proximal and/or distal ends of the mandrel may be modified to allow for easy removal of the mandrel from the stent. In one embodiment, the proximal and distal ends of the flexible mandrel may have bulb-like structures that enable the ends of the mandrel to be grasped using a grasping instrument. In other embodiments, the proximal and distal ends of the flexible mandrel may include apertures that may be grasped using grasping instruments.

In one embodiment, the mandrel may have multiple parts and may be fabricated in a modular fashion that enables the different parts of the mandrel to be removed from inside the stent in multiple steps. In one embodiment, the modular structure includes segments or parts that may be removed individually so as to reduce friction when extracting the mandrel. In one embodiment, the mandrel may be inflatable to provide additional expansion force during deployment of the stent, and during the healing period, if necessary. During extraction, the inflatable mandrel may be deflated to reduce frictional drag.

Referring to FIG. 4A, in one embodiment, the outer sheath 32 carries the stent 50 and the mandrel 56. The outer sheath 32 is preferably flexible. The sheath may be placed over the stent-mandrel combination to allow for atraumatic deployment of the stent and the mandrel in a space under a pharyngeal wall. The sheath may be removed after the stent-mandrel combination has been deployed. Alternatively, the sheath may be bioresorbable and rapidly resorbs in vivo to allow for tissue ingrowth into the stent. Lubricious coatings can be applied to the sheath to aid in atraumatic removal, if necessary. Alternatively, the sheath may include a resorbable polymer such as polylactide, polyglycolide, copolymers thereof, poly(ε-caprolactone), or polydioxanone. In one embodiment, the sheath may remain in the patient after implantation and be rapidly resorbed post-deployment. This particular embodiment decreases the chance of undue tissue trauma that may occur during removal of the sheath. Tissue ingrowth in the form of collagen and epithelial mucosa occurs as the sheath resorbs in situ.

In one embodiment, the stent-mandrel combination may be delivered without a delivery catheter. In this embodiment, the stent-mandrel combination is pulled through the tissue plane through the use of a single or dual armed arced tunneling device or blunt needle. In these embodiments, the device may be passed from a central incision in the pharyngeal wall in opposing directions to locate the stent mandrel within the desired superior and inferior locations or may be passed in one direction from an entry point to an exit point within the pharyngeal wall and/or soft tissues.

Figure 5:
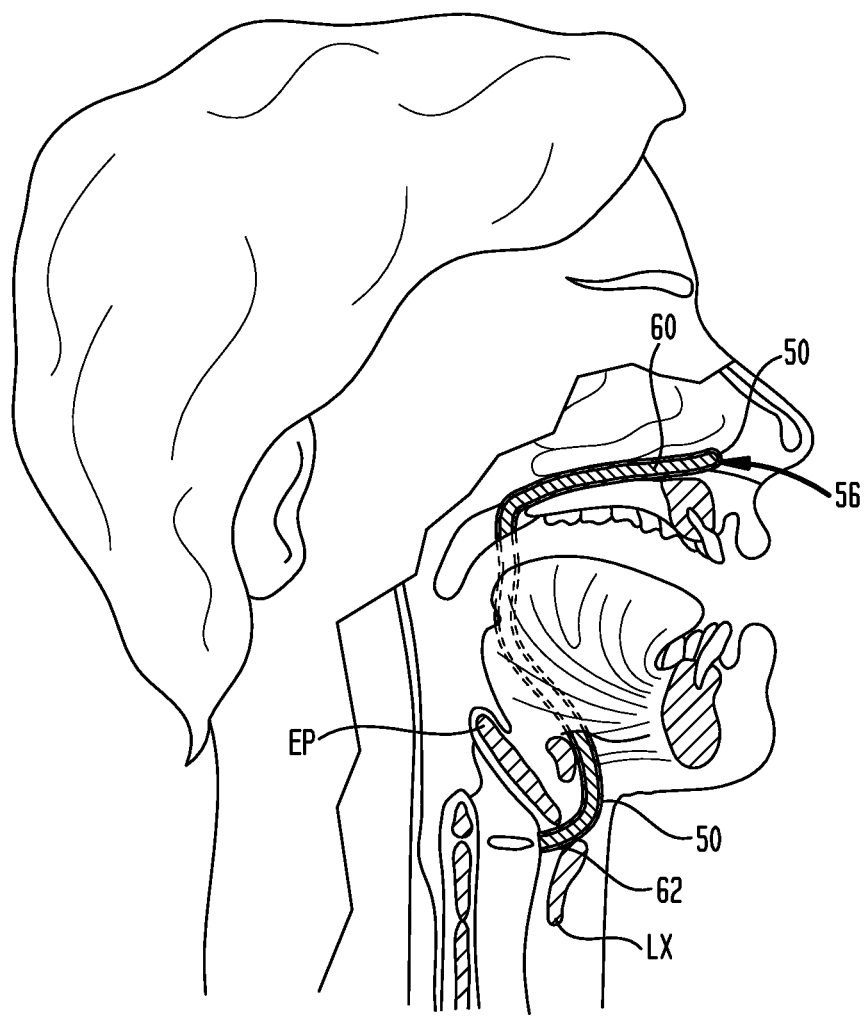
FIGS. 5-7 show a method of implanting an auxiliary airway device for forming an auxiliary airway in a human head, in accordance with one embodiment of the present invention.

FIG. 5 illustrates the stent 50 and the mandrel 56 after being implanted in a human head. The stent and the mandrel may be deployed during an outpatient procedure, or during a procedure requiring a brief hospitalization. In FIG. 5, the mandrel 56 is still in place within the lumen of the stent 50. The proximal end 64 of the stent 50 is positioned within the nasopharynx. The exact location of the proximal end 64 of the stent 50 within the nasopharynx may vary, and is dependent upon the anatomy of the patient. In one embodiment, the proximal end 64 of the stent may be placed in the mouth or the Eustachian tube of the patient. The distal end 66 of the stent 50 is positioned in the hypopharynx region of the pharynx, proximate the epiglottis EP but above the larynx LX.

Figure 6:
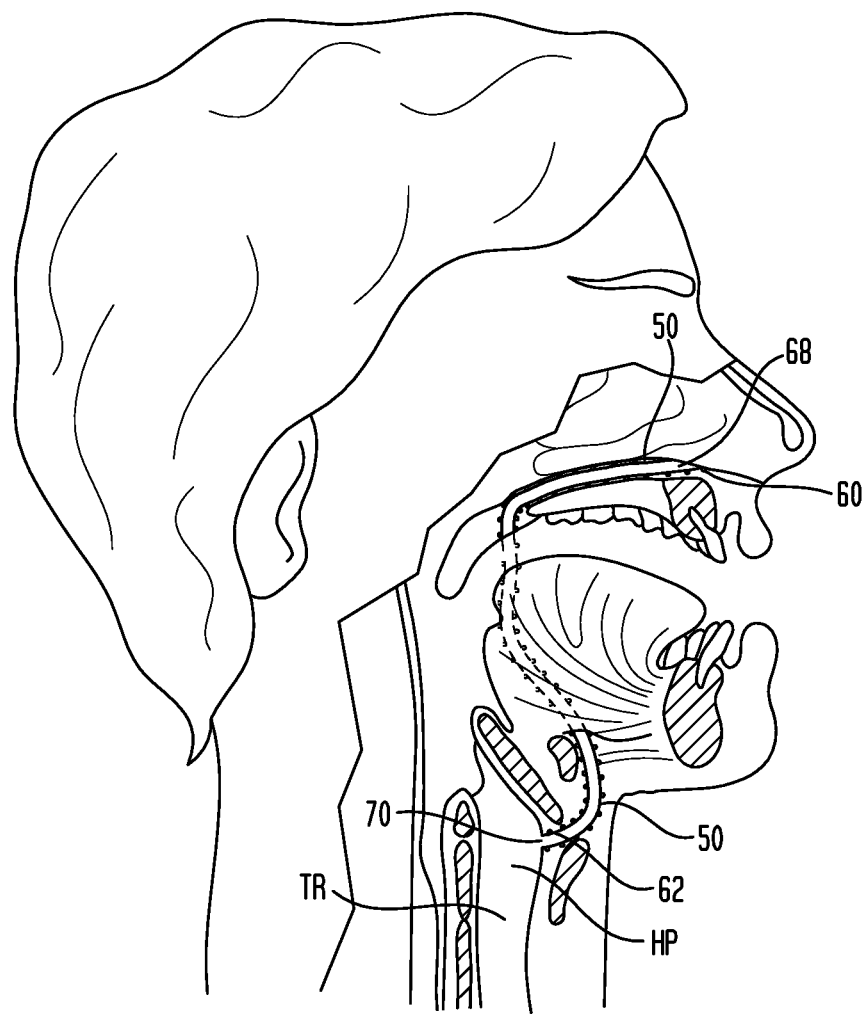

Referring to FIG. 6, after a healing period (e.g. several weeks), the mandrel shown in FIG. 5 is removed so that only the stent 50 remains implanted beneath tissue in the human head. The stent 50 desirably has a first opening 68 at the proximal end 60 of the stent which is positioned within the nasopharynx region. The stent has a second opening 70 at the distal end 62 of the stent 50 that is located within the hypopharynx region HP. The stent 50 having the first and second openings 68, 70 defines an auxiliary airway between the nasopharynx and the hypopharynx that enables a human to breath freely during a sleep apnea episode. Additionally, the auxiliary airway may be sized to provide an alternate pathway that works in conjunction with a partially collapsed airway to minimize the likelihood of a complete airway collapse. In this embodiment, the auxiliary airway is sized to provide a minimum diameter self-supporting airway that prevents the formation of velocity induced pressure reduction within the upper airway.

Figure 7:
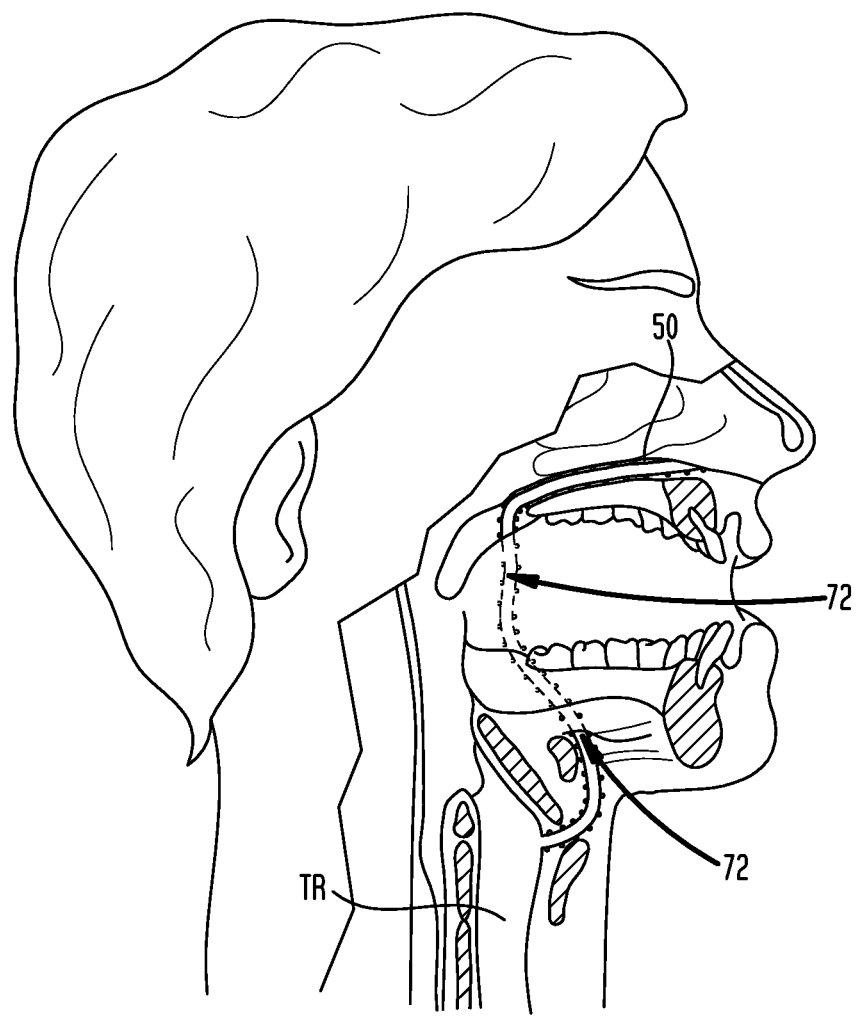

Referring to FIG. 7, after healing has occurred and with the stent 50 in place, an auxiliary airway 72 is formed between the nasopharynx and the trachea TR. In FIG. 7, the tongue has been removed to provide a clearer visualization of the auxiliary airway through the human head. In one embodiment, the auxiliary airway extends between the nasopharynx and the hypopharynx behind either the lateral or posterior pharyngeal walls. In one embodiment, the tunnel originates within the nasal/sinus cavity, descends within the palatine arch, inside of the lower posterior mandible and under the genioglossus muscle. The tunnel then descends inferiorly through the midline of the geniohyoid/digastrics and is directed in a generally inferior/posterior direction to either enter the trachea directly or may be routed through the lateral wall of the pharynx.

In one embodiment, the auxiliary airway device described herein is a stent or tube having a circular cross-section. In other embodiments, however, the auxiliary airway device may be flat or non-cylindrical when viewed in cross-section, and corresponding mandrels having similar shapes may be used. In one embodiment, when viewed in cross-section, auxiliary airway devices and mandrels may have rectangular or elliptical profiles that provide less distortion of the pharyngeal wall. In these embodiments, the implanted device minimizes tenting of tissue and distension of the luminal side of the pharyngeal wall.

FIG. 8 shows a simplified version of the auxiliary airway device shown and described above in FIGS. 5-7. As shown in FIG. 8, in one embodiment, an auxiliary airway is formed using a stent 50 that extends between the nasopharynx region NP and the hypopharynx region HP located below the epiglottis EP and the base of the tongue T. The stent 50 has a proximal end 60 having a first opening 68 that extends through the posterior pharyngeal wall PPW. The stent 50 has a distal end 62 having a second opening 70 that extends through the posterior pharyngeal wall PPW proximate the epiglottis EP and the base of the tongue T. The auxiliary airway formed by the stent 50 bypasses the soft palette SP, the epiglottis EP, and the base of the tongue T of the oropharynx region to overcome the above-described problems associated with obstructive sleep apnea. In FIG. 8, the stent 50 forming the auxiliary airways is shown to pass behind a posterior pharyngeal wall PPW. In highly preferred embodiments, however, the stent passes through a lateral wall of the pharynx.

Referring to FIGS. 9A-9C, in one embodiment, a system for forming an auxiliary airway includes an applicator instrument 130 having an outer sheath 132 with a proximal end 134 and a distal end 136. A distal tip 174 having a guide wire opening 138 is secured to the distal end 136 of the outer sheath 132. The applicator instrument 130 includes a pusher 142 having a proximal end 144 and a distal end 146. The pusher 142 has a central lumen 148 that extends from the proximal end 144 to the distal end 146 thereof.

Referring to FIGS. 9A and 9B, the applicator instrument 130 is utilized for deploying a stent 150. In one embodiment, the stent 150 is a compacted stent graft that is expandable after being deployed within tissue. The stent 150 has a central lumen 158 extending therethrough. The central lumen 158 is desirably in alignment with the guide wire opening 138 and the central lumen 148 of the pusher 142. The applicator instrument 130 also desirably includes a guide wire lumen 176 insertable through the central lumen 148 of the pusher 142, and the central lumen 158 of the expandable stent device 150.

FIG. 9B shows an expanded view of the distal end of the applicator instrument 130 shown in FIG. 9A. The applicator instrument 130 includes the outer sheath 132 having a distal end 136 and the distal tip 174 being secured to the distal end 136 of the outer sheath 132. The expandable stent 150 is disposed within the outer sheath 132. The expandable stent 150 includes stent strut 152 and stent graft material 154. The distal tip 174 includes guide wire opening 138 and the guide wire lumen 176 is in alignment with the guide wire opening 138.

Referring to FIG. 9B, in one embodiment, a guide wire 155 is preferably passed through the guide wire lumen 176 and past the guide wire opening 138 of the distal tip 174. The leading end 178 of the guide wire 155 is passed through target tissue for deploying the stent 150. The distal tip 174 and the outer sheath 132 are advanced over the guide wire 155 for positioning the expandable stent 150 at the preferred implant site within the tissue. Referring to FIG. 9A, once the stent 150 has been advanced to the implant site, the proximal end 134 of the outer sheath 132 is pulled in the direction designated $D_1$ (i.e. toward the proximal end 144 of the pusher 142). The distal end 136 of the outer sheath 132 is thus pulled in the proximal direction for exposing the expandable stent 150 to the tissue at the implant site. Once the expandable stent 150 is exposed beyond the distal end 136 of the outer sheath 132, the stent 150 expands for forming the auxiliary airway within the tissue. After expansion, the expandable stent 150 has a central lumen (not shown) having a larger diameter than the outer diameter of the distal tip 174. As a result, the distal tip 174 may be retracted through the central lumen of the stent 150 and removed from the patient.

Referring to FIGS. 10A and 10B, in one embodiment, a system for forming an auxiliary airway includes a delivery instrument 230 having an outer sheath 232 with a proximal end 234 and a distal end 236. The applicator instrument 230 includes a mandrel 256 having a proximal end 280 and a distal 282. A stent 250 including a stent strut 252 and a stent graft 254 is disposed within the outer sheath 232. The mandrel 256 passes through a lumen or elongated opening in the stent 250. In one embodiment, the distal end 282 of the mandrel 256 extends beyond the distal end 262 of the stent 250 and is attached to a needle 284 having a pointed tip 286.

The stent 250 may be deployed within tissue by inserting the pointed tip 286 of the needle 284 into the tissue and advancing the needle 284 through the tissue. As the needle 284 advances through the tissue, the outer sheath 232, the stent 250, and the mandrel 256 advance with the needle 284. Once the applicator instrument 230 has been advanced so that the stent 250 is located at a desired implant location, the outer sheath 232 may be retracted for implanting the stent 250 in the tissue. In one embodiment, the needle 284 may be broken off from the distal end 236 of the outer sheath 232 and decoupled from the mandrel 256. After the needle 284 is disengaged from the distal end 236 of the outer sheath 232 and the mandrel 256, the needle may be removed from the patient. At about the same time, the outer sheath 232 may be retracted in the direction indicated $D_2$ for deploying the stent 250 and the mandrel 256. The stent 250 and the mandrel 256 preferably remain in place in the tissue during healing. After a healing period, the mandrel 256 may be removed from the stent, preferably in the direction indicated $D_2$. After the mandrel 256 is removed, the stent 250 remains in place for forming an auxiliary airway.

Referring to FIGS. 11A and 11B, in one embodiment, a system for forming an auxiliary airway includes an applicator instrument 330 having a sheath 332 including a proximal end 334 and a distal end 336. The applicator instrument includes a stent 350 having a stent strut 352 and stent graft material 354 surrounding the stent strut 352. The applicator instrument 330 includes a mandrel 356 disposed within a lumen of the stent 350 having a leading end 366 and a trailing end 364. The leading end 366 of the mandrel 356 includes a first eyelet 388, and the trailing 364 of the mandrel 356 includes a second eyelet 390.

In one embodiment, a tunnel is formed through target tissue such as by using a needle or other devices well known to those skilled in the art. In one embodiment, a tether 355 is pulled through the tunnel formed in the tissue. The tether 355 is preferably attached to one or more of the eyelets 388, 390 for pulling the applicator instrument 330 through the tunnel for deploying the stent 350. Once the applicator instrument 330 is located at the desired position within the tissue, the outer sheath 332 may be decoupled from the stent-mandrel combination for implanting the combination in the tissue. In one embodiment, the outer sheath 332 is removed from opposite ends of the tunnel using the tether 355. After the outer sheath 332 is removed, the stent 350 and the mandrel 356 remain in place within the target tissue. After a healing period, the mandrel 356 is retracted from the stent 350 so as to leave the stent in place for forming an auxiliary airway. The mandrel 356 may be removed using the tether 355.

In one embodiment, an auxiliary airway may be created by forming (e.g. cutting) an elongated opening in a pharyngeal wall and placing an auxiliary airway device such as a stent within the opening. The pharyngeal wall may then be closed (e.g. sutured) for covering the auxiliary airway device implanted therein. A first opening is preferably formed in the pharyngeal wall that is in alignment with an opening at a first end of the auxiliary airway device and a second opening is formed in the pharyngeal wall that is in communication with an opening at a second end of the auxiliary airway device.

Figure 12:
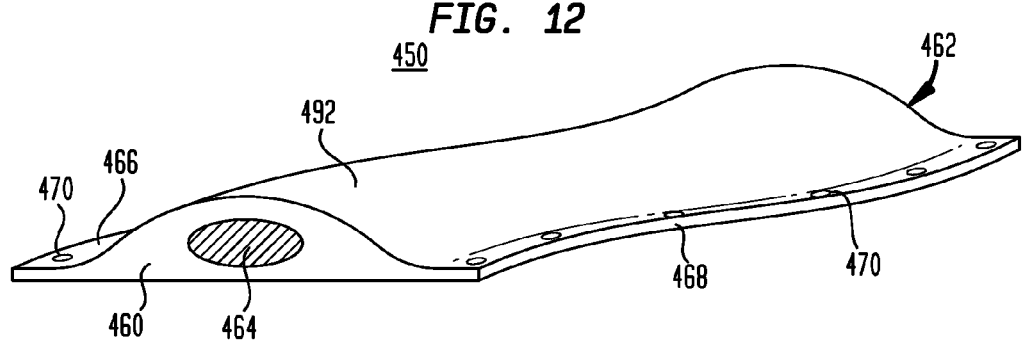
FIG. 12 shows a perspective view of an auxiliary airway device, in accordance with one embodiment of the present invention.

Referring to FIG. 12, in one embodiment, an auxiliary airway device 450 for forming an auxiliary airway includes an elongated main body 492 having a proximal end 460 and a distal end 462. The auxiliary airway device may be made of a broad range of biocompatible materials including biocompatible polymers such as expanded poly-tetrafluoroethylene (e-PTFE), silicone, polyethylene terephalate (PET), non-expanded PTFE, polyurethane, polycarbonate, Polyvinylidene fluoride, and polypropylene. The auxiliary airway device includes at least one central opening 464 extending between the proximal and distal ends 460, 462 thereof. The central opening 464 may be elliptical or elongated in one direction to provide a minimally invasive device that has a lower profile and that minimizes the likelihood of tissue tenting and impinging on the natural airway. The auxiliary airway device 450 includes flared sides 466, 468 that extend laterally from the main body portion 492. The flared lateral sides 466, 468 include a plurality of openings 470 extending along the length of the device 450. The openings 470 provide a mechanism for securing the auxiliary airway device 450 to tissue. In one highly preferred embodiment, the openings 470 provide space for tissue ingrowth for anchoring the auxiliary airway device 450 to tissue.

Figure 13:
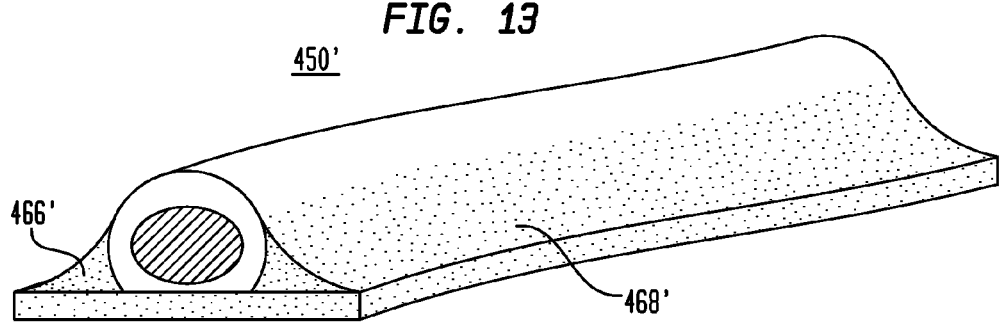
FIG. 13 shows a perspective view of an auxiliary airway device, in accordance with one embodiment of the present invention.

FIG. 13 shows an auxiliary airway device 450' that is generally similar to the device shown and described above in FIG. 12. In FIG. 13 embodiment, the auxiliary airway device 450' includes flared lateral sides 466', 468' having a mesh-like structure that facilitates tissue ingrowth after implantation. The mesh structure can be placed on the side of the auxiliary airway or the bottom or top surfaces.

Figure 14:
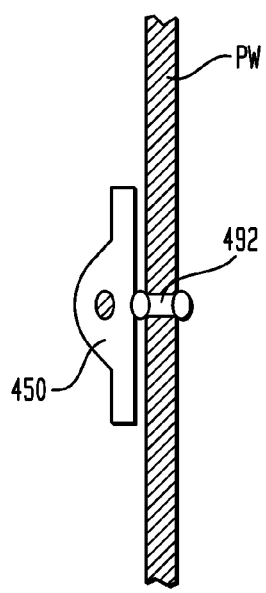
FIG. 14 shows the auxiliary airway device of FIG. 12 implanted beneath a pharyngeal wall, in accordance with one embodiment of the present invention.

FIG. 14 shows the auxiliary airway device 450 of FIG. 12 after the device has been implanted behind a pharyngeal wall PW. The auxiliary airway device 450 preferably has a proximal end including a first opening that is in communication with the nasopharynx and a distal end having a second opening that is below the soft palate and proximate the epiglottis and that is in communication with the trachea of the patient. The openings may be formed using one or more anastomotic couplers 492, as will be described in more detail below.

Figure 15A:
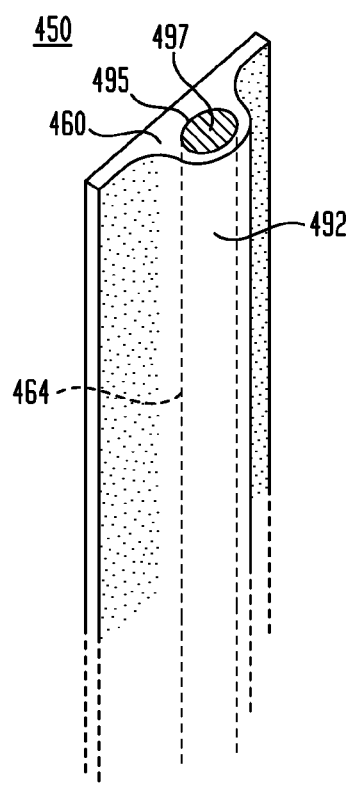
FIGS. 15A-15C show an auxiliary airway device coupled with an opening in a pharyngeal wall via an anastomosis connector, in accordance with one embodiment of the present invention.
Figure 15B:
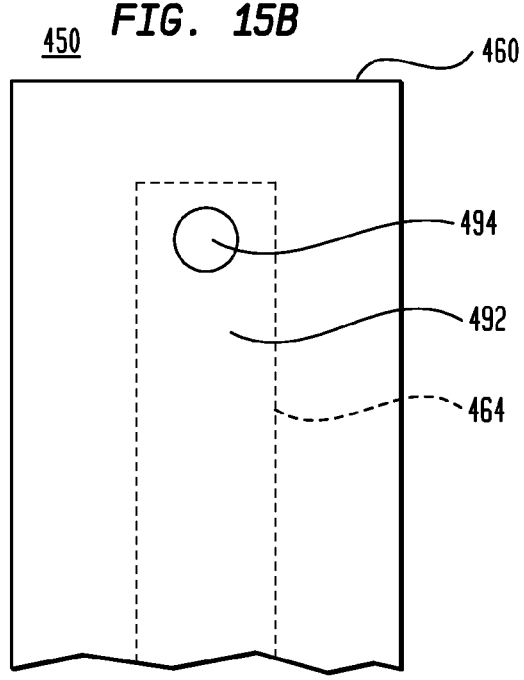
Figure 15C:
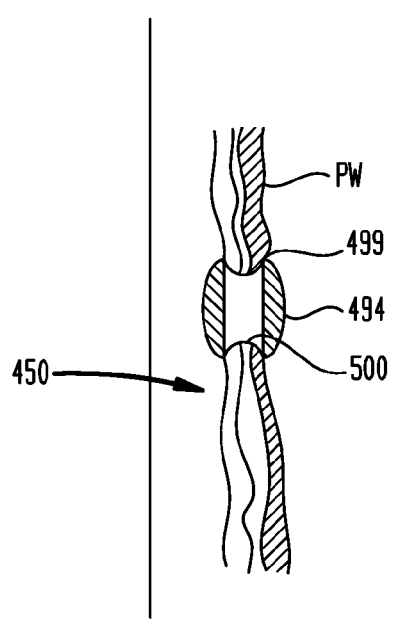

Referring to FIGS. 15A-15C, in one embodiment, an anastomosis is created by forming a first opening 494 in a rear wall of a main body portion 492 of an auxiliary airway device 450. The first opening 494 is desirably in communication with an elongated channel 464 extending between the proximal and distal ends of the auxiliary airway device 450. A first proximal opening 495 at the proximal end 460 of the main body portion 492 may be closed using a plug 497. In other embodiments, glue, spales, sutures, or thermal energy may be used to close off the proximal or distal ends. Referring to FIG. 15C, the first opening 494 in the rear wall of the main body portion 492 is desirably in communication with an opening 499 the pharyngeal wall located in the nasopharynx region, and above the soft tissue normally associated with obstructive sleep apnea episodes. A second opening (not shown) similar to the first opening is desirably formed in a real wall of the main body portion 492. The second opening is preferably adjacent a distal end of the main body portion 492. The second rear wall opening is also desirably in communication with the elongated channel 464 extending through the auxiliary airway device 450. The second opening is desirably in communication with a second opening in the pharyngeal wall located in the hypopharynx region, which is below the oropharynx and proximate the epiglottis.

Referring to FIG. 15C, in one embodiment, an anastomotic connector 500 is used for connecting an opening in the auxiliary airway device 450 with an opening in the pharyngeal wall PW. The anastomotic connector 500 shown in FIG. 15C is coupled with the first rear wall opening 494 (FIG. 15B) formed at a proximal end of the auxiliary airway device 450. A second anastomotic connector may be coupled with a second rear wall opening adjacent a distal end of the auxiliary airway device to provide a second connection between the auxiliary airway device and a second opening in the pharyngeal wall PW. Sutures may also be used to make the anastomoses. In addition, biocompatible glues such as cyanoacrylates may be used with or without sutures to make anastomoses.

Referring to FIG. 16, in one embodiment, an auxiliary airway device 550 includes an elongated main body 592 having a proximal end 560 and a distal end 562 remote therefrom. The main body 592 includes a pair of elongated openings 564A, 564B extending from the proximal end 560 to the distal end 562. The elongated openings 564A, 564B may have a flattened or elliptical appearance when viewed in cross-section. The main body 592 includes flared lateral sides 566, 568 that are adapted to promote tissue ingrowth for anchoring the auxiliary airway device 550 to tissue. The mesh or porous material component may also extend to the top, bottom, or both sides of the auxiliary airway device. One or more anastomoses may be formed with the main body 592. The anastomoses are preferably in communication with at least one of the elongated openings 564A, 564B extending through the main body 592 and openings extending through a pharyngeal wall.

Figure 17A:
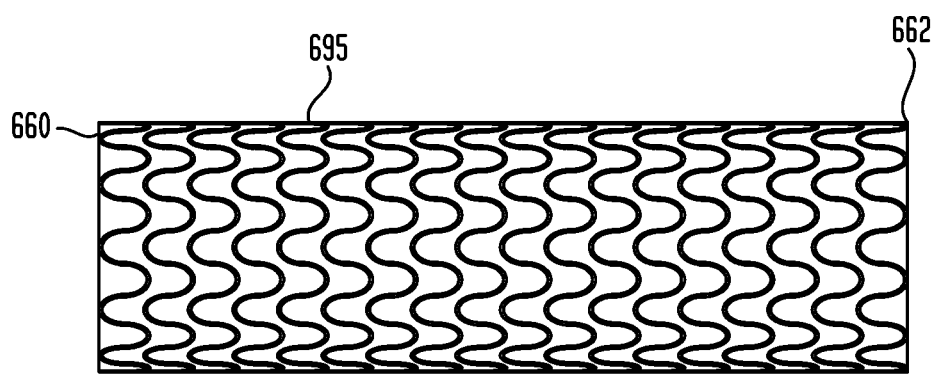
FIGS. 17A-17C show an auxiliary airway device, in accordance with one embodiment of the present invention.
Figure 17B:
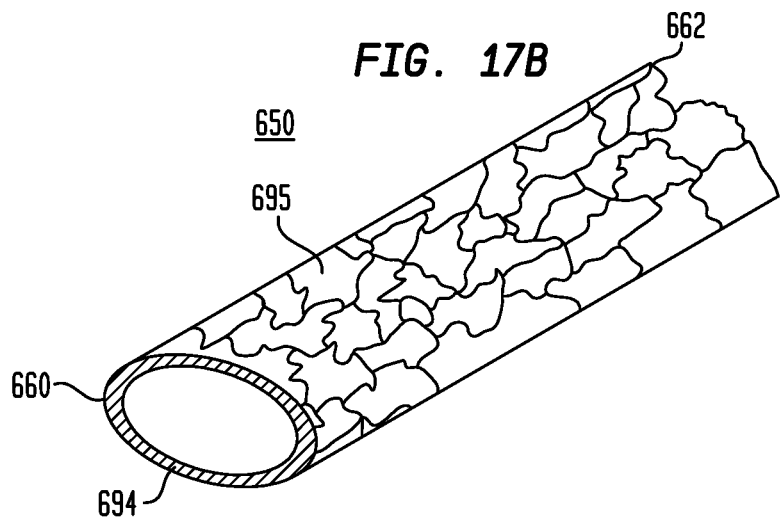
Figure 17C:
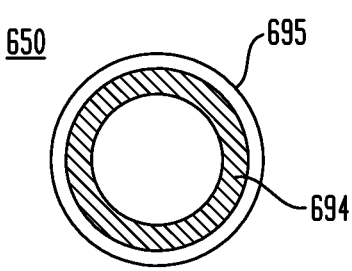

Referring to FIGS. 17A-17C, in one embodiment, an auxiliary airway device 650 has a proximal end 660 and a distal end 662. Referring to FIG. 17B, the auxiliary airway device 650 includes an inner tube 694 that extends between the proximal and distal ends 660, 662, and a stent 695 that surrounds the inner tube 694. In one embodiment, the inner tube 694 is a textile tube and more preferably is an e-PTFE tube, and the stent 695 is preferably a nitinol stent. The stent may also comprise at least in part titanium, tantalum, iron or magnesium alloys, gold, platinum, and stainless steel. In one embodiment, the auxiliary airway device 650 is a nitinol-stented e-PTFE tube wherein the stent is attached to the e-PTFE tube by sutures or glue or the stent is embedded into the wall of the e-PTFE tube. In another embodiment, the auxiliary airway device may be made of a porous textile (PET) graft having a diameter of about 1-5 mm. In preferred embodiments, any of the auxiliary airway devices described above may be used to treat obstructive sleep apnea or hypopnea by implanting the devices in a subcutaneous space for at least a portion of the path of an airway of a mammal.

Figure 18:
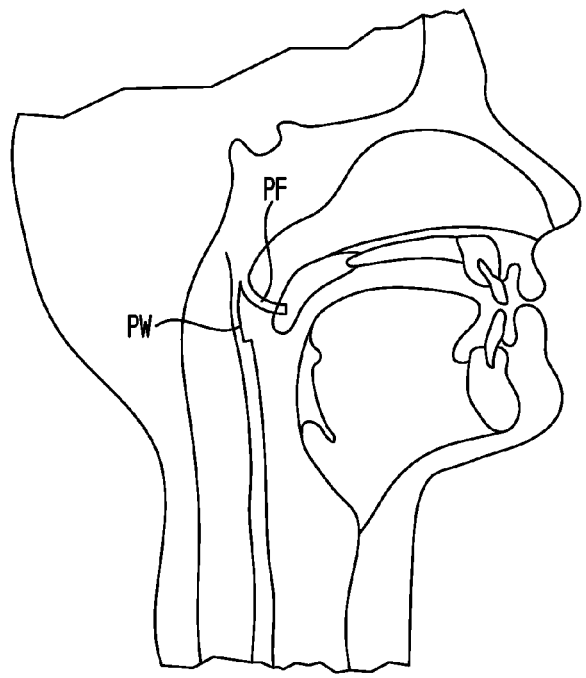
FIG. 18 shows a step of a method for forming an auxiliary airway in a human head, in accordance with one embodiment of the present invention.

Referring to FIG. 18, in one embodiment, a stented airway is placed under a pharyngeal flap PF created from a flap of mucosa obtained from the cheek or the soft palate. In one embodiment, an incision is made in the pharyngeal wall, the auxiliary airway device is put into place under the pharyngeal wall, and the pharyngeal flap PF is sutured in place over the device. The flap may be harvested from numerous sites within the body, including the oral mucosa of the cheek tissues, in the chest, arm, or the pharyngeal wall itself.

Figure 19:
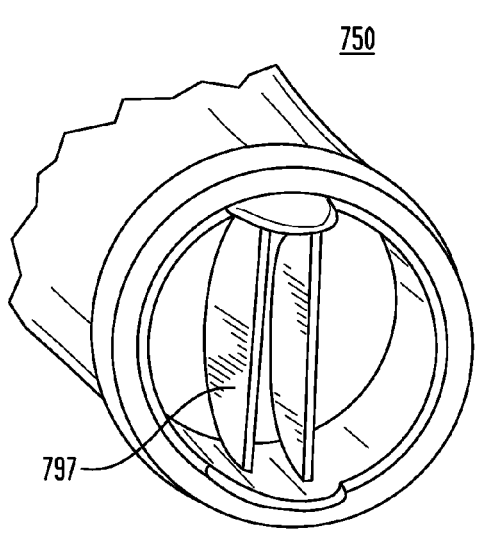
FIG. 19 shows a perspective view of an auxiliary airway device having a valve, in accordance with one embodiment of the present invention.
Figure 20:
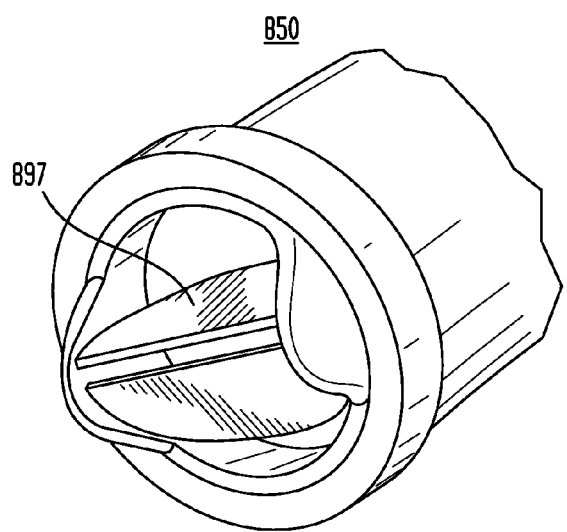
FIG. 20 shows a perspective view of an auxiliary airway device having a valve, in accordance with one embodiment of the present invention.

Referring to FIG. 19, in one embodiment, one or more of the openings of an auxiliary airway device 750 may have valves formed therein. In FIG. 19, the valve is a bi-leaflet valve 797. In other embodiments, the valves may be any suitable valve structure well known to those skilled in the art such as ball valves or flapper-type valves. The use of the valves shown in FIG. 19 will preferably limit the directional flow of air into the auxiliary airway. The valves may be stented or sewn into the openings of the auxiliary airway device before or after manufacture, or before or after implantation. FIG. 20 shows another auxiliary airway device 850 having a flapper-type valve 897 over one of the openings. During the course of exhalation, the valve mechanism is forced closed and the exhaled air is forced out of the natural airway. The valve opens due to the reduced pressure during inhalation. As the valve opens and the auxiliary airway opens, the additional cross sectional area of the auxiliary airway facilitates a reduction in the velocity of the air passing through the pharyngeal lumen. As a result of the mechanics associated with airflow, the reduced velocity results in a greater pressure within the airway. The increased pressure minimizes the opportunity of the airway to be pulled closed through low pressure effects.

In one embodiment, an auxiliary airway device may be formed with regions having varying rigidity. In one particular embodiment, the proximal and/or distal ends of the auxiliary airway device may be less rigid than intermediate portions of the device to provide less support of the surrounding tissue. The tissue surrounding the less rigid ends may naturally supply sufficient pressure to compress the ends of the auxiliary airway device during swallowing and/or during articulation of the tongue during speech. In one embodiment, compression causes a collapse of the ends of the artificial airway to occlude the ends to prevent the entrance of air into the auxiliary airway during the exhalation associated with speech, or the regurgitation of food into the artificial airway during swallowing.

The present invention provides a number of advantages over prior art methods and devices used for treating obstructive sleep apnea syndrome and hypopnea. First, the methods and devices disclosed herein provide for simple surgical procedures that are minimally invasive. Typically, the methods and devices disclosed herein may be utilized during an outpatient procedure. In addition, the methods and devices disclosed herein provide both immediate and long term results for treating obstructive sleep apnea syndrome and hypopnea. The present invention also discloses auxiliary airway devices comprised of materials with known biocompatibility. Furthermore, the present invention provides methods and devices that do not impact the tongue, the hyoid bone, or the soft palate. The methods and devices disclosed herein also have no affect on swallowing or speech after implantation of the auxiliary airway devices.

The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include", "including", and "includes" mean including but not limited to. To facilitate understanding, like reference numerals have been used, where possible, to designate like elements common to the figures.

Although various embodiments disclosed herein relate to use in humans, it is contemplated that the present invention may be used in all mammals, and in all animals having air passages. Moreover, the auxiliary airway devices disclosed herein may incorporate any materials that are biocompatible, as well as any solutions or components that minimize rejection, enhance tissue ingrowth, enhance the formation of mucosal layers, and improve acceptance of the device by a body after the device has been implanted.

While the foregoing is directed to embodiments of the present invention, other and further embodiments of the invention may be devised without departing from the basic scope thereof.

What is claimed is:

1. A system for treating obstructive sleep apnea comprising:
    an elongated conduit adapted to be implanted beneath a pharyngeal wall of a pharynx;
    said elongated conduit having a proximal end adapted to be in communication with a first region of the pharynx and a distal end adapted to be in communication with a second region of the pharynx, wherein a section of said elongated conduit is adapted to extend beneath the pharyngeal wall for bypassing an oropharynx region of the pharynx, and wherein said elongated conduit includes a central lumen defining an inner surface extending along the length of said elongated conduit between the proximal and distal ends thereof; and
    a mandrel insertable within the central lumen of said elongated conduit, said mandrel having an outer surface that contacts the inner surface of the central lumen of said elongated conduit along the length of said elongated conduit for supporting said elongated conduit when implanted beneath the pharyngeal wall, wherein said mandrel has a length that is greater than or equal to the length of said elongated conduit, and wherein the entire length of said elongated conduit is directly supported by said mandrel via contact between the outer surface of said mandrel and the inner surface of the central lumen of said elongated conduit.

2. The system as claimed in claim 1, wherein said elongated conduit has a first opening adjacent the proximal end thereof and a second opening adjacent the distal end thereof, said system further comprising:
    the first opening adjacent the proximal end of said elongated conduit adapted to be in communication with the first opening in the pharyngeal wall; and
    the second opening adjacent the distal end of said elongated conduit adapted to be in communication with the second opening in the pharyngeal wall.

3. The system as claimed in claim 2, wherein the first opening in the pharyngeal wall is in the nasopharynx region of the pharynx and the second opening in the pharyngeal wall is in the hypopharynx region of the pharynx.

4. The system as claimed in claim 2, further comprising:
    a first anastomotic connector adapted for coupling the first opening in the pharyngeal wall with the first opening adjacent the proximal end of said elongated conduit; and
    a second anastomotic connector adapted for coupling the second opening in the pharyngeal wall with the second opening adjacent the distal end of said elongated conduit.

5. The system as claimed in claim 2, wherein said elongated conduit is selected from the group consisting of biocompatible conduits, stents, polymer tubes, and tubes.

6. The system as claimed in claim 1 wherein said elongated conduit has a length of about 5-20 cm and a diameter of about 2-8 mm.

7. The system as claimed in claim 1, further comprising:
    an applicator instrument including an outer sheath with a proximal end and a distal end, the distal end of said outer sheath having a central opening;
    said mandrel is flexible and has a guide wire lumen extending along the length thereof;
    a pusher insertable into said outer sheath for deploying said elongated conduit and said flexible mandrel from the central opening at the distal end of said outer sheath, said pusher having a proximal end, a distal end coupled with a proximal end of said flexible mandrel, and a central lumen extending between the proximal and distal ends of said pusher;
    wherein said flexible mandrel is positioned within said elongated conduit with the guide wire lumen of said flexible mandrel aligned with the central opening at the distal end of said outer sheath and the central lumen of said pusher aligned with both the guide wire lumen of said flexible mandrel and the central opening at the distal end of said outer sheath.

8. The system as claimed in claim 7, wherein the central lumen of said pusher, the guide wire lumen of said flexible mandrel, and the central opening at the distal end of said outer sheath are aligned with one another, and wherein said system further comprises a guide wire insertable into the aligned central lumen of said pusher, the guide wire lumen of said flexible mandrel, and the central opening at the distal end of said outer sheath.

9. The system as claimed in claim 7, further comprising slits extending outwardly from the central opening at the distal end of said outer sheath, wherein said slits define flaps at the distal end of the outer sheath that are normally closed but that are adapted to flex away from one another to provide a larger opening for deploying said elongated conduit and said flexible mandrel.

10. The system as claimed in claim 7, wherein said flexible mandrel has an end having at least one eyelet formed therein and said system further comprises a tether secured to said eyelet for removing said flexible mandrel from said elongated conduit.

11. The system as claimed in claim 7, wherein said flexible mandrel is a modular structure comprising multiple parts that are adapted to be removed individually from inside said elongated conduit for reducing friction as said parts are removed from said elongated conduit.

12. An auxiliary airway for treating obstructive sleep apnea comprising:
    an elongated conduit;
    said elongated conduit having a first opening adapted to be in communication with a first region of a pharynx and a second opening adapted to be in communication with a second region of the pharynx, said elongated conduit including a central lumen having an inner surface that extends along the length of said elongated conduit; and a mandrel disposed within said elongated conduit, said mandrel having an outer surface that contacts the inner surface of the central lumen of said elongated conduit along the length of said elongated conduit for supporting said elongated conduit when implanting said elongated conduit beneath the pharyngeal wall, wherein said mandrel has a length that is greater than or equal to the length of said elongated conduit, and wherein the entire length of said elongated conduit is directly supported by said mandrel via contact between the outer surface of said mandrel and the inner surface of the central lumen of said elongated conduit.

13. The auxiliary airway as claimed in claim 12, wherein the first region is the nasopharynx region of the pharynx and the second region is the hypopharynx region of the pharynx.

14. The auxiliary airway as claimed in claim 12, wherein said elongated conduit is adapted to be implanted beneath a pharyngeal wall.

15. The auxiliary airway as claimed in claim 14, wherein said elongated conduit is adapted to be implanted in a lateral section of the pharyngeal wall.

16. The auxiliary airway as claimed in claim 14, wherein said elongated conduit has a proximal end and a distal end, a proximal opening adjacent the proximal end thereof, and a distal opening adjacent the distal end thereof, and wherein the proximal opening is adapted to be in communication with a first opening in said pharyngeal wall located in the nasopharynx region of the pharynx and the distal opening is adapted to be in communication with a second opening in said pharyngeal wall located in the hypopharynx region of the pharynx.

17. The auxiliary airway as claimed in claim 16, further comprising a first anastomotic connector adapted for coupling the proximal opening of said elongated conduit and the first opening in said pharyngeal wall and a second anastomotic connector adapted for coupling the distal opening of said elongated conduit and the second opening in said pharyngeal wall.

18. The auxiliary airway as claimed in claim 14, wherein said elongated conduit has an intermediate section that is adapted to be implanted beneath the pharyngeal wall, and wherein the intermediate section of said elongated conduit is adapted for bypassing an oropharynx region of the pharynx.

19. The auxiliary airway as claimed in claim 12, wherein said elongated conduit comprises a biocompatible material.

20. The auxiliary airway as claimed in claim 12, wherein said elongated conduit is a structure selected from the group consisting of stents and tubes.

21. The auxiliary airway as claimed in claim 12, further comprising:

an elongated sheath having a proximal end and a distal end, the distal end of said elongated sheath having a central opening;

said mandrel is flexible and has a guide wire lumen extending along the length thereof;

a pusher insertable into said elongated sheath for deploying said elongated conduit and said flexible mandrel from the central opening at the distal end of said elongated sheath, said pusher having a proximal end, a distal end coupled with a proximal end of said flexible mandrel, and a central lumen extending between the proximal and distal ends of said pusher;

wherein said flexible mandrel is positioned within said elongated conduit so that the guide wire lumen of said flexible mandrel is in communication with the central opening at the distal end of said elongated sheath, and the central lumen of said pusher is aligned with both the guide wire lumen of said flexible mandrel and the central opening at the distal end of said outer sheath.

22. The auxiliary airway as claimed in claim 21, wherein the central lumen of said pusher, the guide wire lumen of said flexible mandrel, and the central opening at the distal end of said outer sheath are aligned with one another, and wherein said system further comprises a guide wire insertable into the aligned central lumen of said pusher, the guide wire lumen of said flexible mandrel, and the central opening at the distal end of said outer sheath.

23. The auxiliary airway as claimed in claim 21, further comprising slits extending outwardly from the central opening at the distal end of said elongated sheath, wherein said slits define flaps at the distal end of the elongated sheath that are normally closed but that are adapted to flex away from one another to provide a larger opening for deploying said elongated conduit and said flexible mandrel.

24. A system for treating obstructive sleep apnea comprising:

an applicator instrument including a flexible outer sheath having a proximal end and a distal end, the distal end of said flexible outer sheath having a central opening;

a flexible stent disposed within said flexible outer sheath and adjacent the distal end of said flexible outer sheath, said flexible stent being adapted for implantation beneath a pharyngeal wall of a pharynx, wherein said flexible stent has a proximal end, a distal end, and a central lumen extending between the proximal and distal ends thereof;

a pusher insertable into said flexible outer sheath, said pusher having a proximal end, a distal end, and a central lumen extending between the proximal and distal ends thereof; and a flexible mandrel insertable within the central lumen of said flexible stent for supporting said flexible stent, said flexible mandrel having a guide wire lumen extending along the length thereof, wherein said flexible mandrel is positioned within said flexible stent so that the guide wire lumen of said flexible mandrel is in communication with the central opening at the distal end of said outer sheath, and the central lumen of said pusher is aligned with both the guide wire lumen of said flexible mandrel and the central opening at the distal end of said flexible outer sheath, the mandrel having an outer surface that continuously contacts an inner surface of the central lumen of said flexible stent, wherein the length of said mandrel is greater than or equal to the length of said flexible stent, and wherein the entire length of said flexible stent is directly supported by said mandrel via contact between the outer surface of said mandrel and the inner surface of the central lumen of said flexible stent.

* * * * *